United States Patent
Purdy et al.

(10) Patent No.: US 9,597,480 B2
(45) Date of Patent: Mar. 21, 2017

(54) INTRALUMINAL DEVICES AND SYSTEMS

(71) Applicant: Endophys Holdings, LLC, Dallas, TX (US)

(72) Inventors: Phillip D. Purdy, Maypearl, TX (US); Steven J. Ferry, Maple Grove, MN (US)

(73) Assignee: Endophys Holding, LLC, Dallas, TX (US)

( * ) Notice: Subject to any disclaimer, the term of this patent is extended or adjusted under 35 U.S.C. 154(b) by 0 days.

(21) Appl. No.: 14/876,764

(22) Filed: Oct. 6, 2015

(65) Prior Publication Data

US 2016/0022956 A1    Jan. 28, 2016

Related U.S. Application Data

(63) Continuation of application No. 14/687,761, filed on Apr. 15, 2015, which is a continuation of application (Continued)

(51) Int. Cl.
*A61M 25/00* (2006.01)
*A61B 5/0215* (2006.01)
(Continued)

(52) U.S. Cl.
CPC ......... *A61M 25/0012* (2013.01); *A61B 5/026* (2013.01); *A61B 5/02007* (2013.01); *A61B 5/0215* (2013.01); *A61B 5/0261* (2013.01); *A61B 5/02154* (2013.01); *A61B 5/6852* (2013.01); *A61M 25/005* (2013.01);
(Continued)

(58) Field of Classification Search
CPC ............ A61M 25/0012; A61M 25/005; A61M 25/0097; A61M 2025/0001; A61M 2025/0002; A61M 2025/0003; A61B 5/0215; A61B 5/6852; A61B 5/02158
See application file for complete search history.

(56) References Cited

U.S. PATENT DOCUMENTS 3,782,388 A    1/1974 Page
3,918,019 A    11/1975 Nunn
(Continued)

FOREIGN PATENT DOCUMENTS

DE    3726453    2/1989
EP    0263190    4/1988
(Continued)

OTHER PUBLICATIONS

"Back Break," Article from *Forbes Magazine*, pp. 123-124, Aug. 12, 2002.
(Continued)

*Primary Examiner* — Bhisma Mehta
*Assistant Examiner* — Nilay Shah
(74) *Attorney, Agent, or Firm* — Knobbe, Martens, Olson & Bear, LLP

(57) ABSTRACT

Medical devices, perfusion systems, and methods for detecting a pressure within a space in a subject and for perfusion of fluid into a space in a subject. The space may be a fluid-filled space, or a space that is depleted of fluid due to an obstruction to fluid flow into the space. Methods for forming the medical devices.

19 Claims, 16 Drawing Sheets

Related U.S. Application Data

No. 12/900,360, filed on Oct. 7, 2010, now abandoned.

(60) Provisional application No. 61/249,573, filed on Oct. 7, 2009.

(51) Int. Cl.
  *A61B 5/026*  (2006.01)
  *A61B 5/02*  (2006.01)
  *A61B 5/00*  (2006.01)
  *A61B 17/00*  (2006.01)

(52) U.S. Cl.
  CPC ............... *A61B 2017/00084* (2013.01); *A61B 2090/064* (2016.02); *A61B 2562/12* (2013.01); *A61M 2025/0002* (2013.01); *Y10T 29/49002* (2015.01)

(56) References Cited

U.S. PATENT DOCUMENTS

| | | |
|---|---|---|
| 4,274,423 A | 6/1981 | Mizuno et al. |
| 4,402,694 A | 9/1983 | Ash et al. |
| 4,481,497 A | 11/1984 | Kurtz et al. |
| 4,483,345 A | 11/1984 | Miwa |
| 4,487,206 A | 12/1984 | Aagard |
| 4,593,703 A | 6/1986 | Cosman |
| 4,619,643 A | 10/1986 | Bai |
| 4,660,568 A | 4/1987 | Alderson |
| 4,682,978 A | 7/1987 | Martin |
| 4,691,708 A | 9/1987 | Kane |
| 4,711,246 A | 12/1987 | Alderson |
| 4,722,348 A | 2/1988 | Ligtenberg et al. |
| 4,726,374 A | 2/1988 | Bales |
| 4,787,396 A | 11/1988 | Pidorenko |
| 4,808,157 A | 2/1989 | Coombs |
| 4,809,536 A | 3/1989 | Nishiguchi |
| 4,815,471 A | 3/1989 | Stobie |
| 4,815,472 A | 3/1989 | Wise et al. |
| 4,825,684 A | 5/1989 | Nishiguchi et al. |
| 4,825,876 A | 5/1989 | Beard |
| 4,838,878 A | 6/1989 | Kalt et al. |
| 4,858,615 A | 8/1989 | Meinema |
| 4,873,989 A | 10/1989 | Einzig |
| 4,881,410 A | 11/1989 | Wise et al. |
| 4,901,735 A | 2/1990 | Von Berg |
| 4,904,237 A | 2/1990 | Janese |
| 4,908,693 A | 3/1990 | Nishiguchi |
| 4,911,163 A | 3/1990 | Fina |
| 4,950,232 A | 8/1990 | Ruzicka et al. |
| 4,973,305 A | 11/1990 | Goltzer |
| 4,991,590 A | 2/1991 | Shi |
| 5,018,529 A | 5/1991 | Tenerz et al. |
| 5,050,297 A | 9/1991 | Metzger |
| 5,085,631 A | 2/1992 | Leighton |
| 5,086,777 A | 2/1992 | Hishii |
| 5,098,393 A | 3/1992 | Amplatz et al. |
| 5,108,369 A | 4/1992 | Ganguly et al. |
| 5,113,868 A | 5/1992 | Wise et al. |
| 5,125,058 A | 6/1992 | Tenerz et al. |
| 5,133,358 A | 7/1992 | Gustafson et al. |
| 5,160,323 A | 11/1992 | Andrew |
| 5,178,153 A | 1/1993 | Einzig |
| 5,203,340 A | 4/1993 | Gustafson et al. |
| 5,207,103 A | 5/1993 | Wise et al. |
| 5,218,965 A | 6/1993 | Ring |
| 5,256,146 A | 10/1993 | Ensminger et al. |
| 5,297,437 A | 3/1994 | Schneider |
| 5,297,564 A | 3/1994 | Love |
| 5,318,533 A | 6/1994 | Adams et al. |
| 5,354,271 A | 10/1994 | Voda |
| 5,377,524 A | 1/1995 | Wise et al. |
| 5,378,241 A | 1/1995 | Haindl |
| 5,385,152 A | 1/1995 | Abele et al. |
| 5,397,305 A | 3/1995 | Kawula et al. |
| 5,423,760 A | 6/1995 | Yoon |
| 5,423,849 A | 6/1995 | Engelson et al. |
| 5,425,273 A | 6/1995 | Chevalier |
| 5,437,637 A | 8/1995 | Lieber et al. |
| 5,445,625 A | 8/1995 | Voda |
| 5,449,343 A | 9/1995 | Samson et al. |
| 5,450,853 A | 9/1995 | Hastings et al. |
| 5,470,318 A | 11/1995 | Griffith, III et al. |
| 5,478,331 A | 12/1995 | Heflin et al. |
| 5,487,739 A | 1/1996 | Aebisher et al. |
| 5,520,647 A | 5/1996 | Solar |
| 5,542,936 A | 8/1996 | Razi |
| 5,569,205 A | 10/1996 | Hart et al. |
| 5,613,950 A | 3/1997 | Yoon |
| 5,617,870 A | 4/1997 | Hastings et al. |
| 5,630,802 A | 5/1997 | Moellmann et al. |
| 5,701,905 A | 12/1997 | Esch |
| 5,702,373 A | 12/1997 | Samson |
| 5,704,915 A | 1/1998 | Melsky et al. |
| 5,715,827 A | 2/1998 | Corl et al. |
| 5,731,284 A | 3/1998 | Williams |
| 5,738,650 A | 4/1998 | Gregg |
| 5,800,374 A | 9/1998 | Beyersdorf |
| 5,810,869 A | 9/1998 | Kaplan et al. |
| 5,814,016 A | 9/1998 | Valley et al. |
| 5,830,188 A | 11/1998 | Abouleish |
| 5,833,632 A | 11/1998 | Jacobsen et al. |
| 5,837,234 A | 11/1998 | Gentile |
| 5,846,226 A | 12/1998 | Urmey |
| 5,891,112 A | 4/1999 | Samson |
| 5,902,248 A | 5/1999 | Millar et al. |
| 5,908,385 A | 6/1999 | Chechelski et al. |
| 5,919,221 A | 7/1999 | Miesel |
| 5,928,155 A | 7/1999 | Eggers et al. |
| 5,928,260 A | 7/1999 | Chin et al. |
| 5,931,810 A | 8/1999 | Grabek |
| 5,935,122 A | 8/1999 | Fourkas et al. |
| 5,951,520 A | 9/1999 | Burzynski et al. |
| 5,980,480 A | 11/1999 | Rubenstein et al. |
| 5,980,484 A | 11/1999 | Ressemann et al. |
| 5,984,879 A | 11/1999 | Wallace et al. |
| 5,987,995 A | 11/1999 | Sawatari et al. |
| 6,004,262 A | 12/1999 | Putz et al. |
| 6,004,295 A | 12/1999 | Langer et al. |
| 6,004,310 A | 12/1999 | Bardsley et al. |
| 6,007,478 A | 12/1999 | Siess et al. |
| 6,026,316 A | 2/2000 | Kucharczyk et al. |
| 6,036,654 A | 3/2000 | Quinn et al. |
| 6,042,559 A | 3/2000 | Dobak, III |
| 6,044,845 A | 4/2000 | Lewis |
| 6,061,587 A | 5/2000 | Kucharczyk et al. |
| 6,080,140 A | 6/2000 | Swaminathan et al. |
| 6,090,072 A | 7/2000 | Kratoska et al. |
| 6,106,476 A | 8/2000 | Corl et al. |
| 6,120,457 A | 9/2000 | Coombes et al. |
| 6,120,499 A | 9/2000 | Dickens et al. |
| 6,129,713 A | 10/2000 | Mangosong et al. |
| 6,146,354 A | 11/2000 | Beil |
| 6,162,170 A | 12/2000 | Foley et al. |
| 6,171,252 B1 | 1/2001 | Roberts |
| 6,183,443 B1 | 2/2001 | Kratoska et al. |
| 6,190,349 B1 | 2/2001 | Ash et al. |
| 6,200,336 B1 | 3/2001 | Pavcnik et al. |
| 6,214,029 B1 | 4/2001 | Thill et al. |
| 6,233,488 B1 | 5/2001 | Hess |
| 6,245,026 B1 | 6/2001 | Campbell |
| 6,248,083 B1 | 6/2001 | Smith et al. |
| 6,251,079 B1 | 6/2001 | Gambale et al. |
| 6,251,115 B1 | 6/2001 | Williams et al. |
| 6,272,370 B1 | 8/2001 | Gillies et al. |
| 6,295,990 B1 | 10/2001 | Lewis et al. |
| 6,319,241 B1 | 11/2001 | King et al. |
| 6,328,694 B1 | 12/2001 | Michaeli |
| 6,330,466 B1 | 12/2001 | Hofmann et al. |
| 6,352,530 B1 | 3/2002 | Mangosong |
| 6,379,331 B2 | 4/2002 | Barbut et al. |
| 6,389,902 B2 | 5/2002 | Aigner et al. |
| 6,394,986 B1 | 5/2002 | Millar |

(56) References Cited

U.S. PATENT DOCUMENTS

| | | |
|---|---|---|
| 6,435,189 B1 | 8/2002 | Lewis et al. |
| 6,436,091 B1 | 8/2002 | Harper et al. |
| 6,460,234 B1 | 10/2002 | Gianchandani |
| 6,470,754 B1 | 10/2002 | Gianchandani |
| 6,481,292 B1 | 11/2002 | Reich |
| 6,536,260 B2 | 3/2003 | Williams |
| 6,544,215 B1 | 4/2003 | Bencini et al. |
| 6,616,597 B2 | 9/2003 | Schock et al. |
| 6,644,125 B1 | 11/2003 | Siess et al. |
| 6,652,565 B1 | 11/2003 | Shimada et al. |
| 6,656,153 B1 | 12/2003 | Sakai et al. |
| 6,699,269 B2 | 3/2004 | Khanna |
| 6,758,832 B2 | 7/2004 | Barbut et al. |
| 6,761,715 B2 | 7/2004 | Carroll |
| 6,817,983 B1 | 11/2004 | Millar |
| 6,817,989 B2 | 11/2004 | Svendsen et al. |
| 6,820,487 B2 | 11/2004 | Esashi et al. |
| 6,827,710 B1 | 12/2004 | Mooney et al. |
| 6,886,411 B2 | 5/2005 | Kjellman et al. |
| 6,918,924 B2 | 7/2005 | Lasheras et al. |
| 6,935,999 B2 | 8/2005 | Schock et al. |
| 6,955,675 B2 | 10/2005 | Jain |
| 6,959,608 B2 | 11/2005 | Bly et al. |
| 6,973,835 B2 | 12/2005 | Rangsten et al. |
| 6,988,412 B1 | 1/2006 | Wilner |
| 6,994,695 B1 | 2/2006 | Millar |
| 7,004,936 B2 | 2/2006 | Ryba et al. |
| 7,007,551 B2 | 3/2006 | Zdeblick et al. |
| 7,011,647 B2 | 3/2006 | Purdy et al. |
| 7,013,734 B2 | 3/2006 | Zdeblick et al. |
| 7,014,624 B2 | 3/2006 | Meythaler et al. |
| 7,017,416 B1 | 3/2006 | Liu et al. |
| 7,017,420 B2 | 3/2006 | Kalvesten et al. |
| 7,025,718 B2 | 4/2006 | Williams |
| 7,028,550 B2 | 4/2006 | Zdeblick et al. |
| 7,029,468 B2 | 4/2006 | Honebrink |
| 7,052,452 B2 | 5/2006 | Ulmsten et al. |
| 7,059,195 B1 | 6/2006 | Liu et al. |
| 7,060,038 B2 | 6/2006 | Letort et al. |
| 7,066,031 B2 | 6/2006 | Zdeblick et al. |
| 7,073,387 B2 | 7/2006 | Zdeblick et al. |
| 7,077,812 B2 | 7/2006 | Naghavi |
| 7,112,170 B2 | 9/2006 | Schock et al. |
| 7,118,565 B2 | 10/2006 | Abboud et al. |
| 7,146,865 B2 | 12/2006 | Wilner |
| 7,150,737 B2 | 12/2006 | Purdy et al. |
| 7,156,840 B2 | 1/2007 | Lentz et al. |
| 7,162,925 B2 | 1/2007 | Dietrich |
| 7,162,926 B1 | 1/2007 | Guziak et al. |
| 7,163,535 B2 | 1/2007 | Ryba et al. |
| 7,167,457 B2 | 1/2007 | Vanttinen et al. |
| 7,175,605 B2 | 2/2007 | Tiedtke et al. |
| 7,207,227 B2 | 4/2007 | Rangsten et al. |
| 7,229,403 B2 | 6/2007 | Schock et al. |
| 7,238,168 B2 | 7/2007 | Sirhan et al. |
| 7,263,894 B2 | 9/2007 | Tenerz |
| 7,267,667 B2 | 9/2007 | Houde et al. |
| 7,275,447 B2 | 10/2007 | Krivitski et al. |
| 7,284,441 B2 | 10/2007 | Zdeblick |
| 7,286,879 B2 | 10/2007 | Wallace |
| 7,322,960 B2 | 1/2008 | Yamamoto et al. |
| 7,338,452 B2 | 3/2008 | Shiina et al. |
| 7,351,914 B2 | 4/2008 | Kaneto et al. |
| 7,381,190 B2 | 6/2008 | Sugrue et al. |
| 7,392,716 B2 | 7/2008 | Wilner |
| 7,393,339 B2 | 7/2008 | Zawack et al. |
| 7,398,688 B2 | 7/2008 | Zdeblick et al. |
| 7,452,333 B2 | 11/2008 | Roteliuk |
| 7,455,666 B2 | 11/2008 | Purdy |
| 7,500,947 B2 | 3/2009 | Kucklick et al. |
| 7,503,904 B2 | 3/2009 | Choi |
| 7,505,810 B2 | 3/2009 | Harlev et al. |
| 7,510,533 B2 | 3/2009 | Mauge et al. |
| 7,513,884 B2 | 4/2009 | Miesel et al. |
| 7,515,954 B2 | 4/2009 | Harlev et al. |
| 7,520,858 B2 | 4/2009 | Ofek et al. |
| 7,539,531 B2 | 5/2009 | Camus et al. |
| 7,577,477 B2 | 8/2009 | Allen et al. |
| 7,591,816 B2 | 9/2009 | Wang et al. |
| 7,611,482 B2 | 11/2009 | Naimark et al. |
| 7,632,236 B2 | 12/2009 | Kaneto et al. |
| 7,640,053 B2 | 12/2009 | Verin |
| 7,684,657 B2 | 3/2010 | Donlagic et al. |
| 7,686,781 B2 | 3/2010 | Vinten-Johansen |
| 7,689,071 B2 | 3/2010 | Belleville et al. |
| 7,697,798 B2 | 4/2010 | Lagakos et al. |
| 7,708,705 B2 | 5/2010 | Iddan et al. |
| 7,727,199 B2 | 6/2010 | Fernandes et al. |
| 7,727,228 B2 | 6/2010 | Abboud et al. |
| 7,729,745 B2 | 6/2010 | Maschke |
| 7,731,664 B1 | 6/2010 | Millar |
| 7,787,954 B2 | 8/2010 | Purdy |
| 8,131,353 B2 | 3/2012 | Purdy |
| D711,005 S | 8/2014 | Purdy et al. |
| 8,926,520 B2 | 1/2015 | Purdy et al. |
| 8,961,452 B2 | 2/2015 | Purdy |
| 2001/0035046 A1 | 11/2001 | Williams |
| 2002/0072679 A1 | 6/2002 | Schock |
| 2002/0072680 A1 | 6/2002 | Schock et al. |
| 2002/0091356 A1 | 7/2002 | Barbut et al. |
| 2002/0162399 A1 | 11/2002 | Esashi et al. |
| 2003/0014016 A1 | 1/2003 | Purdy |
| 2003/0029245 A1 | 2/2003 | Izadnegahdar et al. |
| 2003/0083617 A1 | 5/2003 | St. Germain et al. |
| 2003/0093105 A1 | 5/2003 | Huffmaster |
| 2003/0130577 A1 | 7/2003 | Purdy et al. |
| 2003/0171736 A1 | 9/2003 | Bon |
| 2004/0060362 A1 | 4/2004 | Kjellmann et al. |
| 2004/0147433 A1 | 7/2004 | Keep et al. |
| 2004/0168519 A1 | 9/2004 | Kalvensten et al. |
| 2004/0193021 A1* | 9/2004 | Zdeblick ............... A61B 5/036 600/300 |
| 2004/0236223 A1 | 11/2004 | Barnes et al. |
| 2004/0243057 A1 | 12/2004 | Vinten-Johansen |
| 2004/0243115 A1 | 12/2004 | Abboud et al. |
| 2004/0249295 A1 | 12/2004 | Ueno et al. |
| 2004/0249337 A1 | 12/2004 | DiFiore |
| 2004/0254483 A1 | 12/2004 | Zdeblick et al. |
| 2004/0254495 A1 | 12/2004 | Mabary et al. |
| 2004/0260229 A1 | 12/2004 | Meir |
| 2004/0260241 A1 | 12/2004 | Yamamoto et al. |
| 2004/0260328 A1 | 12/2004 | Zvuloni et al. |
| 2005/0004450 A1 | 1/2005 | Ben-Haim et al. |
| 2005/0038328 A1 | 2/2005 | Stoehrer et al. |
| 2005/0043669 A1 | 2/2005 | Rosenberg |
| 2005/0043670 A1 | 2/2005 | Rosenberg |
| 2005/0049451 A1 | 3/2005 | Schock et al. |
| 2005/0070844 A1 | 3/2005 | Chow et al. |
| 2005/0075624 A1 | 4/2005 | Miesel |
| 2005/0103114 A1 | 5/2005 | Bly et al. |
| 2005/0107738 A1 | 5/2005 | Slater et al. |
| 2005/0124971 A1 | 6/2005 | Koch et al. |
| 2005/0148884 A1 | 7/2005 | Parks et al. |
| 2005/0159659 A1 | 7/2005 | Sawan et al. |
| 2005/0160823 A1 | 7/2005 | Zdeblick et al. |
| 2005/0160824 A1 | 7/2005 | Zdeblick et al. |
| 2005/0160825 A1 | 7/2005 | Zdeblick et al. |
| 2005/0160826 A1 | 7/2005 | Zdeblick et al. |
| 2005/0166683 A1 | 8/2005 | Krivitski et al. |
| 2006/0009740 A1* | 1/2006 | Higgins ............... A61M 25/001 604/264 |
| 2006/0030843 A1 | 2/2006 | Lane et al. |
| 2006/0032039 A1 | 2/2006 | Rangsten et al. |
| 2006/0095032 A1 | 5/2006 | Jackson et al. |
| 2006/0100492 A1 | 5/2006 | Hartle et al. |
| 2006/0100639 A1 | 5/2006 | Levin et al. |
| 2006/0106321 A1 | 5/2006 | Lewinsky et al. |
| 2006/0116564 A1 | 6/2006 | Mintchev et al. |
| 2006/0117859 A1 | 6/2006 | Liu et al. |
| 2006/0117871 A1 | 6/2006 | Wilner |
| 2006/0122589 A1 | 6/2006 | Abboud et al. |
| 2006/0129061 A1 | 6/2006 | Kaneto et al. |
| 2006/0130596 A1 | 6/2006 | Wilner |
| 2006/0133715 A1 | 6/2006 | Belleville et al. |

(56) References Cited

U.S. PATENT DOCUMENTS

| | | |
|---|---|---|
| 2006/0135942 A1 | 6/2006 | Fernandes et al. |
| 2006/0137457 A1 | 6/2006 | Zdeblick |
| 2006/0142783 A1 | 6/2006 | Lewis et al. |
| 2006/0149141 A1 | 7/2006 | Sheets |
| 2006/0149218 A1 | 7/2006 | Slater et al. |
| 2006/0173365 A1 | 8/2006 | Thompson |
| 2006/0189928 A1 | 8/2006 | Camus et al. |
| 2006/0211944 A1 | 9/2006 | Mauge et al. |
| 2006/0211945 A1 | 9/2006 | Mauge et al. |
| 2006/0211946 A1 | 9/2006 | Mauge et al. |
| 2006/0243061 A1 | 11/2006 | Krivitski et al. |
| 2006/0244177 A1 | 11/2006 | Kaneto et al. |
| 2006/0258981 A1 | 11/2006 | Eidenschink |
| 2006/0271029 A1 | 11/2006 | Abboud et al. |
| 2006/0278248 A1 | 12/2006 | Viswanathan |
| 2006/0281986 A1 | 12/2006 | Orilla et al. |
| 2006/0287569 A1 | 12/2006 | Schock et al. |
| 2007/0027393 A1 | 2/2007 | Williams et al. |
| 2007/0028698 A1 | 2/2007 | Guziak et al. |
| 2007/0032783 A1 | 2/2007 | Abboud et al. |
| 2007/0055142 A1 | 3/2007 | Webler |
| 2007/0062546 A1 | 3/2007 | Viswanathan et al. |
| 2007/0066890 A1 | 3/2007 | Maschke |
| 2007/0093710 A1 | 4/2007 | Maschke |
| 2007/0129667 A1 | 6/2007 | Tiedtke et al. |
| 2007/0135712 A1 | 6/2007 | Maschke |
| 2007/0135736 A1 | 6/2007 | Addington et al. |
| 2007/0151348 A1 | 7/2007 | Zdeblick et al. |
| 2007/0161882 A1 | 7/2007 | Pappone |
| 2007/0173777 A1* | 7/2007 | Murphy ............... A61M 39/26 604/247 |
| 2007/0179492 A1 | 8/2007 | Pappone |
| 2007/0191717 A1 | 8/2007 | Rosen et al. |
| 2007/0197922 A1 | 8/2007 | Bradley et al. |
| 2007/0213669 A1 | 9/2007 | Eskuri et al. |
| 2007/0250050 A1 | 10/2007 | Lafontaine |
| 2007/0255090 A1 | 11/2007 | Addington et al. |
| 2007/0270782 A1 | 11/2007 | Miesel et al. |
| 2007/0282211 A1 | 12/2007 | Ofek et al. |
| 2008/0009837 A1 | 1/2008 | Miesel |
| 2008/0009925 A1 | 1/2008 | Abboud et al. |
| 2008/0027332 A1 | 1/2008 | Bradley |
| 2008/0033316 A1 | 2/2008 | Kassab et al. |
| 2008/0097383 A1 | 4/2008 | Vinten-Johansen |
| 2008/0132826 A1 | 6/2008 | Shadduck et al. |
| 2008/0142783 A1 | 6/2008 | Emerson et al. |
| 2008/0161794 A1 | 7/2008 | Wang et al. |
| 2008/0194933 A1 | 8/2008 | Kunze |
| 2008/0214983 A1 | 9/2008 | Mauge et al. |
| 2008/0228167 A1 | 9/2008 | Mittermeyer et al. |
| 2008/0243074 A1 | 10/2008 | Miesel et al. |
| 2008/0255467 A1 | 10/2008 | Acker et al. |
| 2008/0269581 A1 | 10/2008 | Wood et al. |
| 2009/0013791 A1 | 1/2009 | Zdeblick et al. |
| 2009/0018504 A1* | 1/2009 | Pile-Spellman ......... A61F 7/12 604/113 |
| 2009/0024016 A1 | 1/2009 | Zhang et al. |
| 2009/0036754 A1 | 2/2009 | Pons et al. |
| 2009/0069714 A1 | 3/2009 | Eichmann et al. |
| 2009/0082678 A1 | 3/2009 | Smith |
| 2009/0088609 A1 | 4/2009 | Schmitz-Rode et al. |
| 2009/0088735 A1 | 4/2009 | Abboud et al. |
| 2009/0105799 A1 | 4/2009 | Kemat et al. |
| 2009/0118637 A1 | 5/2009 | Kassab et al. |
| 2009/0125007 A1 | 5/2009 | Splinter |
| 2009/0138007 A1 | 5/2009 | Govari et al. |
| 2009/0156953 A1 | 6/2009 | Wondka et al. |
| 2009/0156960 A1 | 6/2009 | Mauge et al. |
| 2009/0171201 A1 | 7/2009 | Olson |
| 2009/0177183 A1 | 7/2009 | Pinkernell et al. |
| 2009/0192450 A1 | 7/2009 | Miesel et al. |
| 2009/0202195 A1 | 8/2009 | Lagakos et al. |
| 2009/0209950 A1 | 8/2009 | Starksen |
| 2009/0234378 A1 | 9/2009 | Escudero et al. |
| 2009/0270739 A1 | 10/2009 | Hatib et al. |
| 2009/0287118 A1 | 11/2009 | Malek |
| 2009/0299356 A1 | 12/2009 | Watson |
| 2010/0094209 A1 | 4/2010 | Drasler et al. |
| 2010/0106087 A1 | 4/2010 | Evans et al. |
| 2010/0106140 A1 | 4/2010 | Odland et al. |
| 2010/0113939 A1 | 5/2010 | Mashimo et al. |
| 2010/0113945 A1 | 5/2010 | Ryan |
| 2010/0113949 A1 | 5/2010 | Sathyanarayana |
| 2010/0113967 A1 | 5/2010 | Bobo |
| 2010/0114063 A1 | 5/2010 | Recinella et al. |
| 2010/0114083 A1 | 5/2010 | Sharma |
| 2010/0121159 A1 | 5/2010 | Burnett et al. |
| 2010/0121213 A1 | 5/2010 | Giftakis et al. |
| 2010/0121214 A1 | 5/2010 | Giftakis et al. |
| 2010/0125211 A1 | 5/2010 | Stahmann et al. |
| 2010/0137736 A1 | 6/2010 | Addington et al. |
| 2011/0092955 A1 | 4/2011 | Purdy et al. |
| 2015/0025396 A1 | 1/2015 | Purdy et al. |
| 2015/0112211 A1 | 4/2015 | Purdy |
| 2015/0112212 A1 | 4/2015 | Purdy |
| 2015/0289816 A1 | 10/2015 | Purdy et al. |
| 2015/0367105 A1 | 12/2015 | Purdy |
| 2016/0022956 A1 | 1/2016 | Purdy et al. |

FOREIGN PATENT DOCUMENTS

| | | |
|---|---|---|
| EP | 0454264 | 10/1991 |
| EP | 1062959 | 11/2004 |
| WO | WO 97/44082 | 11/1997 |
| WO | WO 98/38953 | 9/1998 |
| WO | WO 98/57603 | 12/1998 |
| WO | WO 99/20334 | 4/1999 |
| WO | WO 00/51669 | 9/2000 |
| WO | WO 01/54766 | 8/2001 |
| WO | WO 02/068036 | 9/2002 |
| WO | WO 2008/021437 | 2/2008 |

OTHER PUBLICATIONS

"Keeping it Cool," Article from *Health Communities, United Hospital*, 11:1, 8, Winter 2003.

Amar et al., "Microcatheterization of the cervical epidural space via lumbar puncture: Technical note," *Neurosurgery*, 48(5):1183-1187, 2001.

Blomberg, "A method for eipiduroscopy and spinaloscopy. Presentation of preliminary results," *Acta Anaesthesiol Scand*, 29(1):113-116 (1985).

Blomberg, "Fibrous structures in the subarachnoid space: a study with spinaloscopy in autopsy subjects," *Anesth Analg*, 80(5):875-879 (1995).

Delhaas, "Extradural and subarachnoid catheterization using the Seldinger technique," *Br J Anaesth*, 76(1):149-150 (1996).

Eguchi et al., "Endoscopy of spinal cord and posterior fossa by a lumbar percutaneous approach: endoscopic anatomy in cadavers," *Minim Invasive Neurosurg*, 42(2):74-78 (1999).

Eguchi et al., "Endoscopy of the spinal cord: cadaveric study and clinical experience," *Minim Invasive Neurosurg*, 42(3):146-151 (1999).

Fries et al., "Biportal Neuroendoscopic Microsurgical Approaches to the Subarachnoid Cisterns. A Cadaver Study," *Minim Invas Neurosurg*, 39:99-104 (1996).

Hamada et al., "Microcatheter intrathecal urokinase infusion into cisterna magna for prevention of cerebral vasospasm," *Stroke*, 31:2141-2148 (2000).

Karakhan et al., "Use of intracranial endoscopy in morphologic studies," *Arkh Anat Gistol Embriol*,98(1):75-82, (1990).

Miyamoto et al., "The development of spinal endocope using a flexible optic fiber," *No To Shinkei*, 41(12):1233-1238 (1989) abstract on p. 1238.

Stefanov et al., "A new method for transcutaneous coaxial neuroendoscopy," *Anat Embryol*, 194(4):319-326 (1996).

Suzukawa et al., Percutaneous fiberoptic spinal laser endoscopy, *J Clin Laser Med Surg*, 8(6):27-30 (1990).

Tanaka et al., "Endoscopic treatment of symptomatic spinal subarachnoid cysts," *AJR Am J Roentgenol*, 169(6):1719-1720 (1997).

(56) References Cited

OTHER PUBLICATIONS

Uchiyama et al., "Ultrafine flexible spinal endoscope (Myeloscope) and discovery of an unreported subarachnoid lesion," Spine, 23(21):2358-2362 (1998).
Vinas et al., "Microanatomical basis for the third ventriculostomy," *Minim Invasive Neurosug*, 39(4):116-121 (1996).
U.S. Appl. No. 14/627,990, filed Feb. 20, 2015, Sheath With Sensing Capabilities.
U.S. Appl. No. 15/138,127, filed Apr. 25, 2016, Methods of Using a Dual-Lumen Sheath In Intraluminal Procedures.
U.S. Appl. No. 10/328,373, filed Dec. 23, 2002, Guide Catheter for Introduction Into the Subarachnoid Space and Methods of Use Thereof.
U.S. Appl. No. 12/900,360, filed Oct. 7, 2010, Pressure-Sensing Medical Devices, Systems and Methods, and Methods of Forming Medical Devices.
U.S. Appl. No. 14/687,761, filed Apr. 15, 2015, Device Configured for Real-Time Pressure Sensing.
U.S. Appl. No. 14/553,922, filed Nov. 25, 2014, Transducer Interface System and Method.
U.S. Appl. No. 14/554,546, filed Nov. 26, 2014, Transducer Interface System and Method.
U.S. Appl. No. 14/335,525, filed Jul. 18, 2014, Blood Pressure Analysis System and Method.

\* cited by examiner

FIG. 1A
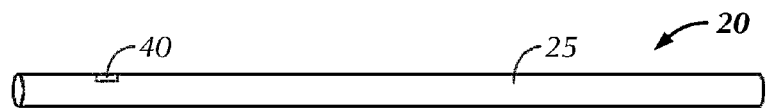
FIG. 1B
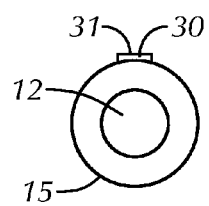   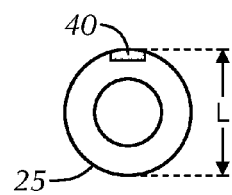   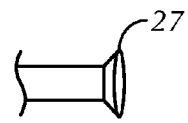
FIG. 1C       FIG. 1D       FIG. 1E

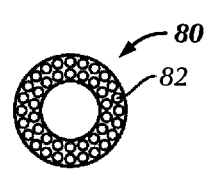
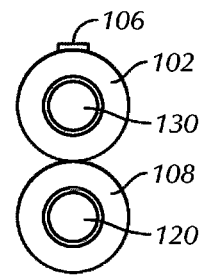
FIG. 4  FIG. 5C
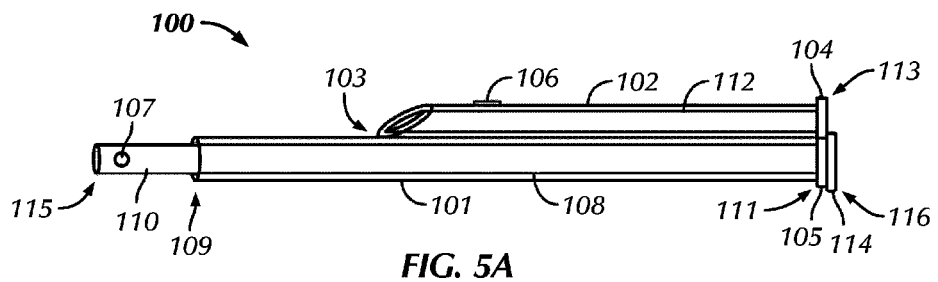
FIG. 5A
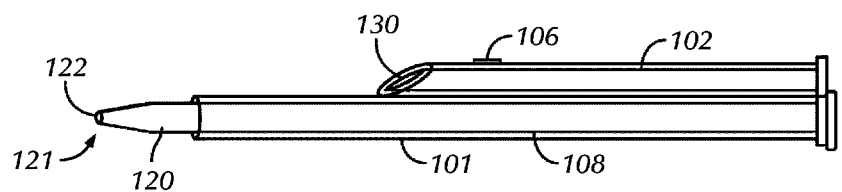
FIG. 5B

INTRALUMINAL DEVICES AND SYSTEMS

CROSS-REFERENCE TO RELATED APPLICATIONS

This application is a continuation of U.S. patent application Ser. No. 14/687,761, filed Apr. 15, 2015, which is a continuation of U.S. patent application Ser. No. 12/900,360, filed Oct. 7, 2010, which claims priority to U.S. Provisional Application No. 61/249,573 filed Oct. 7, 2009, the entireties of all of which are incorporated by reference without disclaimer.

BACKGROUND

Field

The invention relates generally to medical devices, perfusion systems, and combinations of medical devices and perfusion systems configured to detect fluid pressure in a fluid-filled space or space normally occupied by fluid and/or to transfer fluid to or from a space in a subject. The invention also relates to perfusion systems configured to be used to perfuse a fluid into a site in a subject, such as a site downstream to an arterial or venous occlusion in a subject. The invention further relates to methods of perfusing a fluid into a subject that has an obstruction to fluid flow by employing a medical device, perfusion system, or combination of medical device and perfusion system to perfuse fluid downstream to a site of obstruction to fluid flow. The obstruction to fluid flow may be, for example, an obstruction to blood flow in a blood vessel, such as a cerebral artery. The invention also relates to methods of manufacturing the present medical devices.

Description of the Related Art

Examples of medical devices that include pressure sensors and reperfusion devices include those disclosed in U.S. Pat. Nos. 5,701,905, 5,800,374, 6,042,559, 6,044,845, 6,295,990, 6,435,139, and 7,520,858, and U.S. Patent Application Pub. Nos. 2008/0142783, 2008/0161794, 2008/0228167, 2009/0125007, 2010/0114063.

SUMMARY

Methods for incorporating one or more sensors (e.g., pressure sensors) into conduits like catheters, sheaths, and hubs for either are disclosed. Some embodiments of the methods include creating passageways for the transmission lines for the sensors.

Some embodiments of the present methods include forming an elongated body having a wall that defines a first lumen, a stiffener embedded in the wall, and a sensor lumen positioned in the wall, where the sensor lumen is not in direct fluid communication with the first lumen and does not impinge on the first lumen, the elongated body has a first end and a second end, and the first lumen extends from the first end to the second end such that both the first and second ends are open; and positioning a sensor at least partially in the sensor lumen. In some embodiments, the method also includes connecting a hub to the elongated body, the hub containing a first lumen in communication with the first lumen of the elongated body, a valve configured to seal the first lumen of the hub, and a second lumen in communication with the sensor lumen of the elongated body. The hub may have multiple pieces. The hub lumens may be positioned in separate pieces or the same piece.

Some embodiments of the present methods include positioning one or more of: a first lumen mandrel; a stiffener; a second lumen mandrel; a first lumen tube; a second lumen tube; and a shrink wrap material such that the stiffener is outside of the first lumen mandrel, the first lumen tube is outside of the stiffener, the shrink wrap material is outside of the first lumen tube, and both the second lumen mandrel and the second lumen tube are inside of the shrink wrap material, thereby forming a combination; heating the combination such that a melting temperature of the first lumen tube is reached and such that an activation temperature of the shrink wrap material is reached, the heating being sufficient to form an elongated body having a wall defining a first lumen, the elongated body also having a second lumen positioned in the wall; after the heating, removing the second lumen mandrel leaving the second lumen formed at least in part by the second lumen tube; and positioning a sensor at least partially in the second lumen; where the elongated body has a first end and a second end, and the first lumen extends from the first end to the second end such that both the first and second ends are open. The heating may be accomplished through an infrared heater.

Medical devices made using the present methods are also disclosed. Some embodiments of the present medical devices include an elongated body having a wall that defines a first lumen, a stiffener embedded in the wall, and a sensor lumen positioned in the wall; and a sensor positioned at least partially in the sensor lumen; where the sensor lumen is separate from the first lumen so as not to be in direct fluid communication with the first lumen and does not impinge on the first lumen, the elongated body has a first end and a second end, and the first lumen extends from the first end to the second end such that both the first and second ends are open.

Some embodiments of the present medical devices include a body configured as a hub for connection to an elongated tube, the body including a primary lumen, a side arm that includes a flushing lumen that is in direct fluid communication with the primary lumen, and an embedded transmission line that is not in direct fluid communication with the flushing lumen or the primary lumen within the body; and a valve configured to seal the primary lumen.

Some embodiments of the present medical devices and perfusion systems can be used to detect fluid pressure in a space and to transmit fluid to or from a space in a subject. The medical devices and perfusion systems have a wide application in the treatment of subjects with an obstruction to fluid flow, such as an obstruction to blood flow in a blood vessel or an obstruction of a visceral organ.

The present medical devices may have an elongated body having a passageway, a downstream end, and a proximal end; and a pressure sensor attached to the elongated body, the pressure sensor having a length along any axis that is not greater than 2 mm, the pressure sensor being configured to detect a fluid pressure and output one or more signals representative of the detected fluid pressure. Whether an end is "proximal" or "distal" is determined relative to the position of a user. For example, if an elongated body is inserted by a user into a subject, the "distal end" is the end that is farthest away from the user and the "proximal end" is the end that is closest to the user. Some embodiments are further defined as having a device length extending from the distal end of the elongated body to the proximal-most exposed portion of the proximal end of the elongated body, where the device length is between 10 cm and 160 cm. In some embodiments, the device length is between 60 cm and 140 cm. At least a portion of the elongated body of the medical device has a outer diameter of 3 French (1.0 mm) to 10 French (3.3 mm). The French size will in part depend on the application. For example, for applications that involve infusion of fluid into a cerebral artery, the outer diameter of the medical devices will range from 3 French to 4 French. Larger diameters may be used for infusion of fluid into larger vessels (such as a femoral artery, carotid artery) or a hollow visceral organ (such as urethra, ureter, or bladder) or when used as an introducer sheath.

In some embodiments, the pressure sensor is configured to have a thickness of between 1 micron and 500 microns. The pressure sensor may have a thickness of between 1 micron and 100 microns. The pressure sensor may be configured to communicate a signal corresponding to fluid pressure via radiofrequency signals or other forms of wireless communication. In some embodiments, the pressure sensor has a width of 10 microns to 2.0 mm, a length of 10 microns to 2.0 mm, and a thickness of 10 microns to 1.0 mm.

The present medical devices may further include a hub coupled to or integral with the proximal end of the elongated body. The hub can be configured in any manner known to those of ordinary skill in the art. For example, the hub may be configured to interlock with a second medical device such as a tubular medical device for transfer of a fluid from one site (such as the passageway of the medical device) to a second site.

The present medical devices may optionally include a side arm having a side arm passageway in communication with the passageway of the elongated body, where the pressure sensor is not exposed to the passageway of the elongated body. In some embodiments, the medical device further includes a stopcock coupled to or integral with the side arm. The side arm may have a proximal end coupled to or integral with a hub.

In some embodiments, the medical device includes an introducer slidably positioned in the passageway of the elongated body, the introducer having a tapered distal tip. The introducer is configured to facilitate insertion of the medical device into a fluid-filled site in a subject, such as a blood vessel. The introducer may be positioned in the passageway of the elongated body such that the distal tapered tip protrudes from the distal end of the elongated body. The proximal end of the introducer may be configured to contact or interlock with the proximal end of the elongated body such that the position of the introducer is secured with the distal tapered tip protruding from the distal end of the elongated body. Such stabilization facilitates the use of the introducer to insert the medical device into a fluid-filled space in a subject.

Some embodiments of the present medical devices include: (1) sheath that includes a sheath elongated body having a passageway, a distal end, and a proximal end; a side arm having a side arm passageway in communication with the passageway of the sheath elongated body; and a sheath pressure sensor attached to the sheath elongated body, the sheath pressure sensor being configured to detect a fluid pressure and output one or more signals representative of the detected fluid pressure; (2) an introducer that includes an introducer elongated body having a proximal end and a distal end that includes a tapered tip, the introducer being configured to be slidably positioned within the passageway of the sheath elongated body; and (3) a catheter that includes a catheter elongated body having a catheter passageway, a distal end, and a proximal end coupled to or integral with a hub; and a catheter pressure sensor attached to the catheter elongated body, the catheter pressure sensor being configured to detect a fluid pressure and output one or more signals representative of the detected fluid pressure; where the catheter is configured to be slidably positioned within the passageway of the sheath elongated body when that passageway is not occupied by the introducer.

The sheath may have a sheath length extending from the distal end of the sheath elongated body to the proximal-most exposed portion of the proximal end of the sheath elongated body, the sheath length being between 10 cm and 150 cm. In some embodiments, the sheath length is between 60 cm and 90 cm. At least a portion of the sheath elongated body may have an outer diameter of 5 French (1.67 mm) to 10 French (3.3 mm).

The catheter may have a catheter length extending from the distal end of the catheter elongated body to the proximal-most exposed portion of the proximal end of the catheter elongated body, the catheter length being between 70 cm and 160 cm. In further embodiments, such as embodiments utilized for insertion into the cerebral vasculature of a subject, the catheter length is between 120 cm and 140 cm. At least a portion of the catheter elongated body has an outer diameter of 3 French (1 mm) to 7 French (2.3 mm).

In some embodiments, the passageway of the sheath elongated body has a diameter that is 0.5 to 2 mm larger than the outer diameter of the catheter that is slidably configured to be positioned within the passageway of the sheath elongated body. In other embodiments, the passageway of the sheath elongated body is 0.5 to 1 mm larger than the outer diameter of the catheter that is slidably configured to be positioned within the passageway of the sheath elongated body.

The introducer may include an introducer passageway configured to receive a guidewire. In some embodiments, the medical device further includes a guidewire slidably positioned in the introducer passageway. The guidewire may be any guidewire known to those of ordinary skill in the art. The guidewire typically includes a proximal end and a distal end. The length of the guidewire, which is the distance between the proximal end and the distal end, is typically greater than the length of the introducer.

In some embodiments of the present medical devices that include a sheath, and the passageway of the sheath is thermally insulted. Thermal insulation of the passageway of the sheath may be performed using any method known to those of ordinary skill in the art, including any of the methods described below for thermally insulating a passageway of a catheter.

The catheter elongated body may optionally include a region that thermally insulates the catheter passageway. For example, a fluid that is cooled below the body temperature of a subject may be infused into a space in a subject using the catheter. Thermal insulation of the catheter passageway facilitates retention of temperature of the infused fluid. A separate pump may be used to pump a coolant through the catheter wall (or the sheath wall in instances where the catheter is slidably positioned within the sheath) in a closed loop system. Any method known to those of ordinary skill in the art may be used to insulate the catheter passageway.

In some embodiments, the medical device includes: (1) a first sheath comprising a first sheath elongated body having a first sheath passageway, a distal end, and a proximal end coupled to a valve, the first sheath having a length extending from the distal end of the first sheath elongated body to the proximal-most exposed portion of the first sheath elongated body; (2) a second sheath that includes a second sheath elongated body having a second sheath passageway, a distal end, and a proximal end coupled to or integral with a hub, the second sheath having a length extending from the distal end of the second elongated body to the proximal-most exposed portion of the second elongated body, the length of the first sheath being greater than the length of the second sheath, the second sheath being couplable to the first sheath so that, in use during a procedure, the distal end of the second sheath elongated body will be proximal of the distal end of the first sheath elongated body; (3) a catheter including a catheter elongated body configured to be positionable in the first sheath passageway, the catheter having a distal end and a proximal end coupled to or integral with a hub; (4) a first pressure sensor attached to the first sheath or the second sheath, the first pressure sensor being configured to detect a fluid pressure and output one or more signals representative of the detected fluid pressure; (5) a second pressure sensor attached to the catheter, the second pressure sensor being configured to detect a fluid pressure and output one or more signals representative of the detected fluid pressure; (6) a first introducer positionable in the first sheath passageway, the first introducer having a tapered distal tip; and (7) a second introducer positionable in the second sheath passageway.

The first introducer may include an introducer passageway configured to receive a guidewire, and the medical device further includes a guidewire positionable in the introducer passageway. In some embodiments, the distal tip of the second introducer is configured to align with the distal end of the second sheath elongated body to form a substantially flush end surface.

Further embodiments include perfusion systems that include: (1) a sheath including a sheath elongated body having a passageway, a distal end, and a proximal end; a side arm having a side arm passageway in communication with the passageway of the sheath elongated body; a sheath pressure sensor attached to the sheath elongated body, the sheath pressure sensor being configured to detect a fluid pressure and output one or more signals representative of the detected fluid pressure; (2) a catheter including a catheter elongated body having a catheter passageway, a distal end, and a proximal end coupled to or integral with a hub; and a catheter pressure sensor attached to the catheter elongated body, the catheter pressure sensor being configured to detect a fluid pressure and output one or more signals representative of the detected fluid pressure; where the catheter is configured to be slidably positioned within the passageway of the sheath elongated body; and (3) a device including a detector system configured to receive one or more signals from the sheath pressure sensor and/or the catheter pressure sensor to determine and/or display a value corresponding to each detected fluid pressure; and a pump coupled to the side arm and to the catheter, the pump configured to facilitate the transfer of fluid from the side arm to the catheter.

The pump may be configured to facilitate the transfer of fluid from the side arm to the catheter using any method known to those of ordinary skill in the art. For example, the pump may utilize a roller on a piece of tubing to facilitate pumping of fluids. In other embodiments, a chamber with a compressor facilitates transfer of fluids. A power syringe may be employed such as a power injector pump used for angiographic procedures. Other examples of pumps contemplated include diaphragm-type mechanisms to fill a chamber and then empty it, with valves to control the directionality of flow.

The device may further be configured to reduce temperature of the fluid that is being transferred from the side arm to the catheter. Any method known to those of ordinary skill in the art may be used to reduce temperature of the transferred. For example, the device may include a thermoregulator that functions to reduce temperature of the fluid that is being pumped from the side arm to the catheter.

The perfusion system may include any of the medical devices as set forth in this disclosure. In some embodiments, the perfusion system further includes a thermoregulator. The thermoregulator is configured to cool blood that has passed from the side arm to the catheter. The thermoregulator may be separate or integral to the detector system. The thermoregulator may further include a monitor that displays temperature of the fluid that has passed from the side arm to the catheter. In some embodiments, an ice bath is configured to be a thermoregulator.

Some embodiments of the present perfusion systems include: (1) a first sheath including a first sheath elongated body having a first sheath passageway, a distal end, and a proximal end coupled to a valve, the first sheath having a length extending from the distal end of the first sheath elongated body to the proximal-most exposed portion of the first sheath elongated body; (2) a second sheath including a second sheath elongated body having a second sheath passageway, a distal end, and a proximal end coupled to or integral with a hub, the second sheath having a length extending from the distal end of the second sheath elongated body to the proximal-most exposed portion of the second sheath elongated body, the length of the first sheath being greater than the length of the second sheath, the second sheath being couplable to the first sheath so that, in use during a procedure, the distal end of the second sheath elongated body will be proximal of the distal end of the first sheath elongated body; (3) a catheter comprising a catheter elongated body configured to be positionable in the first sheath passageway, the catheter having a distal end and a proximal end coupled to or integral with a hub; (4) a first pressure sensor attached to the first sheath or the second sheath, the first pressure sensor being configured to detect a fluid pressure and output one or more signals representative of the detected fluid pressure; (5) a second pressure sensor attached to the catheter, the second pressure sensor being configured to detect a fluid pressure and output one or more signals representative of the detected fluid pressure; (6) a first introducer positionable in the first sheath passageway, the first introducer having a tapered distal tip; a second introducer positionable in the second sheath passageway; and (7) a device having a detector system configured to receive one or more signals from the first pressure sensor and/or the second pressure sensor to determine and/or display a value corresponding to each detected fluid pressure; and a pump coupled to the side arm and to the catheter, the pump configured to facilitate the transfer of fluid from the second sheath passageway to the catheter.

The device components may be incorporated into a single unit, or may be in multiple units. In some embodiments, a control system facilitates coordinating of the separate components of the device.

Also disclosed are methods of perfusing a fluid in a subject that has an obstruction to fluid flow, including: inserting a first elongated body having a passageway into the subject; inserting a catheter through the passageway and advancing the catheter in a downstream (distal) direction through the obstruction; detecting a fluid pressure downstream of the obstruction with a pressure detector attached to the catheter; detecting a fluid pressure upstream of the obstruction with a pressure detector attached to the first elongated body; withdrawing blood from the subject; and perfusing the blood through the catheter and to a location downstream of the obstruction if a fluid pressure detected downstream of the obstruction satisfies a safety check. In some embodiments, the blood withdrawn from the subject is withdrawn out of a side port of the first elongated body. In further embodiments, the blood withdrawn from the subject is withdrawn out of a second elongated body coupled to the first elongated body.

The subject may be a patient with an obstruction to blood flow. For example, the patient may have a plaque in an artery or a thrombus in a vein. In particular embodiments, the patient has an obstruction to flow in a cerebral artery, resulting in a stroke. The stroke may be a non-hemorrhagic stroke. One embodiment may be a method of treating a patient with a stroke that involves reperfusion of blood beyond a site of arterial occlusion in a cerebral artery. Blood obtained from the hub of the second catheter may be perfused through the passageway of the catheter. Restoration of perfusion to levels that will sustain tissue without infarction is one purpose of the present methods.

In some embodiments, the fluid that is perfused into the subject is cooled fluid. For example, in methods that concern the treatment of a patient with a stroke, reperfusion of cooled blood provides for preservation of brain tissue to slow cerebral metabolism sufficiently that metabolic demands of the brain are decreased. Lowered tissue temperature lowers the requirements of oxygen and glucose to maintain tissue viability, thus reducing the likelihood of infarction and permanent damage. Other means to slow cerebral metabolism that are contemplated for inclusion in the present methods include infusion of barbiturates through the catheter to induce a "barbiturate coma" in portions of the brain that are undergoing reperfusion. Other means to slow tissue metabolism are contemplated for optional inclusion in the present methods.

In some embodiments, a catheter pressure sensor monitors fluid pressure downstream (distal) to a site of obstruction to blood flow. Infusion of fluid through the catheter will be controlled such that the intravascular pressure encountered by the catheter pressure sensor will not exceed the fluid pressure as detected by the sheath pressure sensor. Such monitoring of pressure provides for a safety mechanism to limit the prospect that pressure will rise unexpectedly to levels that will result in vascular compromise, such as arterial rupture. Hence, the monitoring of fluid pressure proximal and distal to a site of vascular occlusion is integral to the safe function of the reperfusion system.

If fluid pressure as measured by the catheter pressure sensor equals pressure as measured by the catheter sheath, a safety mechanism may be incorporated into the device such that pumping of fluid from the second sheath (or side arm) is halted or slowed.

The present methods may further include, while at least a portion of the first elongated body is surrounding at least a portion of the catheter, directing a cooled solution through the first elongated body for a period of time while perfusing the blood through the catheter. In some embodiments, the perfusing is controlled based on one or more of the fluid pressure detected downstream of the obstruction and the fluid pressure detected upstream of the obstruction.

Some embodiments of the present methods that include the dual sheath system further include flushing a cooled solution such as heparinzed saline along the catheter between the catheter and the sheath when the catheter is slidably positioned within the sheath and blood is flowing through catheter to a location downstream of the obstruction. This flushing with cooled fluid may be particularly useful if the blood traveling through the catheter is cooled in that it will help to maintain that cooled state. The flushing may be accomplished in any suitable manner (e.g., with a compressible bulb, a plungable syringe, a pump separate from the pump that advances the blood, etc.). The flushing may also help to prevent thrombus formation along the course of the catheter passing through the sheath.

Some embodiments of the present methods anticipate administering one or more additional therapies directed at the treatment of a subject with an obstruction to flow of a fluid. For example, a subject with an obstruction to blood flow may receive a pharmacological agent such as an agent that facilitates clot dissolution. Other therapeutic agents contemplated for administration include anticoagulants, medications to prevent seizure occurrence, and antibiotics. Also, devices which remove a clot ("Merci") or aspirate a clot ("Penumbra") exist currently for stroke therapy and may be used in conjunction with the present method. In some embodiments, the additional treatment includes stent placement or angioplasty.

Some aspects of the present kits include any of the present medical devices or perfusion systems in suitable packaging. For example, the kit may include a present medical device in a hermetically sealed package and instructions for use. Further embodiments of the kits include a present perfusion system in suitable packaging, with instructions for use. Medical device and perfusion system components, such as catheters, sheaths, introducers, and guidewires, may be packaged separately in the kit in hermetically sealed containers or may be packaged in the same hermetically sealed container.

Some embodiments of the present kits include a pump for administration of a hypothermic flushing solution into a passageway of a lumen of a catheter, sheath, or side arm of the present medical devices.

Any embodiment of any of the present medical devices, perfusion systems, methods and kits may consist of or consist essentially of—rather than comprise/include/contain/have—the described features and/or steps. Thus, in any of the claims, the term "consisting of" or "consisting essentially of" may be substituted for any of the open-ended linking verbs recited above, in order to change the scope of a given claim from what it would otherwise be using the open-ended linking verb.

BRIEF DESCRIPTION OF THE DRAWINGS

The following drawings illustrate by way of example and not limitation. Identical reference numbers do not necessarily indicate an identical structure. Rather, the same reference number may be used to indicate a similar feature or a feature with similar functionality, as may non-identical reference numbers. Every feature of each embodiment is not always labeled in every figure in which that embodiment appears, in order to keep the figures clear.

FIG. 1A is a side view of an embodiment of the present medical devices.

FIG. 1B is a side view of another embodiment of the present medical devices.

FIG. 1C is a cross-sectional view of the device depicted in FIG. 1A through the pressure sensor.

FIG. 1D is a cross-sectional view of the device depicted in FIG. 1B through the pressure sensor.

FIG. 1E is a side view of the proximal end of an embodiment of the present medical devices that includes a hub at the proximal end of the medical device.

FIG. 4 is a cross-sectional view of one embodiment of the present medical devices depicting a plurality of spaces within the wall of the elongated body that provide for thermoregulation of fluid within the passageway of the elongated body.

FIG. 5A is a side view of an embodiment of the present medical devices having a first sheath and a second sheath, with a catheter slidably positioned within the passageway of the first sheath.

FIG. 5B is a side view of an embodiment of the present medical devices having a first sheath and a second sheath as in FIG. 5A, with a first introducer slidably positioned within the first sheath passageway and a second introducer slidably positioned within the second sheath passageway.

FIG. 5C is a cross-sectional view of the medical device shown in FIG. 5B, depicting a first introducer within the first sheath passageway and a second introducer within the second sheath passageway.

DETAILED DESCRIPTION

Figure 2:
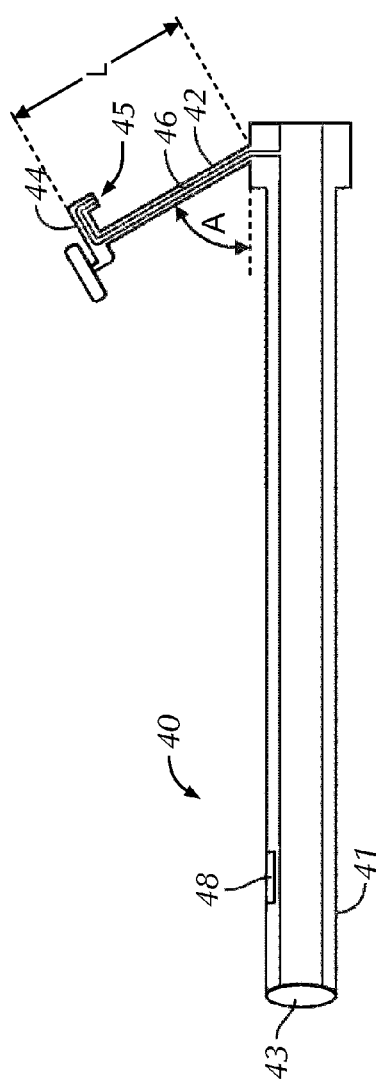
FIG. 2 is a side view of an embodiment of the present medical devices showing a proximal end that includes a side arm with a stopcock.

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a medical device, a perfusion system, a kit, or a method that "comprises," "has," "contains," or "includes" one or more recited elements or steps possesses those recited elements or steps, but is not limited to possessing only those elements or steps; it may possess elements or steps that are not recited. Likewise, an element of a medical device, a perfusion system, a kit, or a method that "comprises," "has," "contains," or "includes" one or more recited features possesses those features, but is not limited to possessing only those features; it may possess features that are not recited. Furthermore, a medical device, perfusion system, or a structure of one or both of these that is configured in a certain way must be configured in at least that way, but also may be configured in a way or ways that are not specified.

The terms "a" and "an" are defined as one or more than one unless this disclosure explicitly requires otherwise. The terms "substantially" is defined as at least close to (and includes) a given value or state. The term "coupled" is defined as connected, although not necessarily directly, and not necessarily mechanically; two items that are "coupled" may be integral with each other.

In some embodiments, the present medical devices may be used to detect a fluid pressure in a space within a subject, to continually monitor fluid pressure in such a space, and/or to deliver a fluid to a space in a subject to which fluid flow has been reduced or eliminated due to the presence of an obstruction, such as a patient whose blood flow is obstructed due to a thrombus, plaque, or embolus. Embodiments of the present medical devices and perfusion systems may be used to concurrently monitor fluid pressure downstream or distal to a site of obstruction to fluid flow and upstream of the obstruction site (or otherwise in a location where the fluid is flowing normally) and to provide for controlled infusion of blood and/or other fluid distal to a site of obstruction. For example, a user can position an embodiment of the present medical devices in a blood vessel of a subject, position the medical device in a manner such that a first pressure sensor is distal to a site of obstruction in a blood vessel and a second pressure sensor is proximal to the site of obstruction. Based on information concerning fluid pressure that is detected from one or both pressure sensors, fluid such as blood can be delivered in a controlled manner distal to the site of obstruction to fluid flow to provide for controlled reperfusion. Embodiments of the present medical devices and perfusion systems therefore allow for restoration of perfusion of fluid or blood downstream to a site of obstruction in a blood vessel or other space through which fluid flows in a subject. Restoration of blood flow distal to a site of obstruction in a blood vessel, such as a cerebral blood vessel, enables both the reperfusion of ischemic tissue and the metabolic protection of the brain tissue in the distribution of the occluded vessel.

Medical Devices

FIG. 1A shows one embodiment of the present medical devices, which takes the form of a catheter. Medical device 10 comprises an elongated body 15 having a passageway 12, a distal end 14, and a proximal end 16, and a pressure sensor 30 attached to the elongated body 15. The pressure sensor 30 has a length along any axis that is not greater than 2 mm (meaning that a straight line that intersects the outer boundary at any two points will not have a length greater than 2 mm between those two points), and is configured to detect a fluid pressure and output one or more signals representative of the detected fluid pressure.

Any pressure sensor known to those of ordinary skill in the art that has the capability to generate a signal or signals representative of a detected fluid pressure is contemplated as a pressure sensor for use with at least some embodiments of the present medical devices and present perfusion systems. Non-limiting examples of pressure sensors that may be included in the present medical devices and perfusion systems include those set forth in U.S. Patent Appl. Pub. No. 2008/0228167, which is specifically incorporated by reference in its entirety. For example, some particular information concerning pressure sensors can be found in paragraphs [0010]-[0016], [0024]-[0027], [0030], and FIGS. 1-5 of U.S. Patent Appl. Pub. No. 2008/00228167. Other examples of pressure sensors include those set forth in U.S. Patent Appl. Pub. Nos. 20070135718, 20090024015, 20050187487, and 20030018273, each of which is specifically incorporated by reference in its entirety.

Elongated body 15 has length L that extends from the most distal portion of distal end 14 and the proximal-most exposed portion (e.g., not covered by a hub, valve, or the like) of proximal end 16 that ranges from 10 cm to 160 cm. In other embodiments, length L ranges from 60 cm to 140 cm. In further embodiments, length L ranges from 80 cm to 140 cm. In other embodiments, length L ranges from 100 cm to 140 cm. Length L may be 10 cm, 15 cm, 20 cm, 25 cm, 30 cm, 35 cm, 40 cm, 45 cm, 50 cm, 55 cm, 60 cm, 65 cm, 70 cm, 75 cm, 80 cm, 85 cm, 90 cm, 95 cm, 100 cm, 105 cm, 110 cm, 115 cm, 120 cm, 125 cm, 130 cm, 135 cm, 140 cm, 145 cm, 150 cm, 155 cm, 160 cm, or any range derivable within any of the aforementioned lengths.

Embodiments of the present medical devices can be fabricated to be a variety of lengths. Length L may be selected by one of ordinary skill in the art depending upon the application of the medical device and/or the size of the subject. For example, a medical device with length L of 15 cm may be chosen for treatment of an obstruction in a femoral artery. Longer lengths, such as 125 cm to 135 cm, may be selected for treatment of an obstruction to cerebral blood flow in a subject. For treatment of a carotid artery obstruction in a patient, length L of 60 cm to 90 cm may be selected. The foregoing are examples, and are not intended to limit the application of the present medical devices.

Passageway 12 may have a uniform diameter, or a diameter that varies along the length of the passageway. For example, in some embodiments, the passageway diameter decreases near the distal end of the elongated body. In some embodiments, the passageway diameter varies from 0.25 mm to 1 cm. In other embodiments, the passageway diameter ranges from 0.5 mm to 5 mm. In further embodiments, the passageway diameter ranges from 0.5 mm to 2 mm.

In some embodiments, elongated body 15 may have a uniform outer diameter along length L of the medical device, and in other embodiments may have an outer diameter that varies. The outer diameter D of elongated body 15 may range from 3 French (1.0 mm) to 10 French (3.3 mm). In some embodiments, the outer diameter D of elongated body 15 ranges from 3 French to 7 French. In some embodiments, outer diameter D of medical device 10 ranges from 3 French to 6 French. Outer diameter of medical device 10 may be 1 French, 2 French, 3 French, 4 French, 5 French, 6 French, 7 French, 8 French, 9 French, 10 French, 11 French, 12 French, or any range of outer diameters derivable within these specific outer diameters. The outer diameter will largely depend on the application. For example, it is contemplated that for treatment of occlusion of a cerebral artery in a human subject, that outer diameter of medical device 10 will not be larger than 4 French.

Proximal end 14 of the elongated body may have a rounded edge or may have a blunt edge.

Pressure sensor 30 is depicted near distal end 14 of medical device 10. The diameter of the pressure sensor along any axis of pressure sensor is not greater than 2 mm. For example, the diameter of pressure sensor may range from 0.5 mm to 2.0 mm. In other embodiments, the diameter of the pressure sensor ranges from 1.0 mm to 2.0 mm.

Pressure sensor 30 is configured to detect a fluid pressure and output one or more signals representative of the detected fluid pressure. In some embodiments, the pressure sensor detects fluid pressure continually (real-time), and provides a continual output of signals that are representative of the detected fluid pressure. In other embodiments, the pressure sensor detects fluid pressure intermittently, such as once a minute, twice a minute, three times a minute, four times a minute, or five or more times a minute. Pressure sensor 30 is configured to output a signal corresponding to fluid pressure using any method known to those of ordinary skill in the art. For example, the pressure sensor may detect fluid pressure in response to a signal it receives from a remote controller, or it may be internally programmed to detect fluid pressure at a given rate. The rate at which fluid pressure is detected and/or the rate at which a signal or signals representative of the detected fluid pressure are outputted from the sensor may range, for example, from 5 hertz to 200 hertz, 20 hertz to 100 hertz, or 40 hertz to 80 hertz. In some embodiments, the rate for detection and/or for outputting signal(s) is 60 hertz. In other embodiments, the rate for detection and/or for outputting signal(s) may be 250 hertz or higher.

The one or more signals are transmitted to at least a detector. The transmission of signals from the pressure sensor to the detector may be accomplished in any suitable manner known to those of ordinary skill in the art, including in "wired" or "wireless" fashion. Embodiments of the present pressure sensors may also be configured to receive power in any suitable manner known to those of ordinary skill in the art, including in wired or wireless fashion.

Medical device 10 may include a hub 27. FIG. 1E depicts an embodiment of the present medical devices with hub 27 attached to the distal end of the elongated body, illustrating that, in some embodiments, a hub is separately coupled to the distal end of the elongated body of the medical device and secured in position using any method known to those of ordinary skill in the art. In further embodiments, the hub is integrally fabricated with the elongated body of medical device 10. Hub 27 is represented generically, and can have any suitable configuration known to those of ordinary skill in the art, such as a luer lock configuration that is configured for coupling to a second medical device. The second medical device may be, for example, tubing configured for transferring blood or fluid from the lumen of the tubing through the hub of the medical device and into the passageway of the medical device. In some embodiments, device 10 includes a valve at proximal end 16 of elongated body 15. The valve may be attached to the elongated body using any technique known to those of ordinary skill in the art.

FIG. 2 depicts medical device 40, another embodiment of the present medical devices, which takes the form of a sheath. Medical device 40 includes side arm 42 having a side arm passageway 46 in communication with the passageway of elongated body 41 of medical device 40. Medical device 40 also includes pressure sensor 48. Pressure sensor 48 is not in contact with passageway 43 of medical device 40. In medical device 40, side arm 42 forms an angle A with elongated body 41 of medical device 40. The angle A is less than 90 degrees in medical device 40. The angle A may be more or less than 90 degrees. In some embodiments, angle A ranges from 30 degrees to 150 degrees. In some other embodiments, angle A ranges from 45 degrees to 135 degrees. Angle A may be 30, 35, 40, 45, 50, 55, 60, 65, 70, 75, 80, 85, 90, 95, 100, 105, 110, 115, 120, 125, 130, 135, 140, 145, or 150 degrees, or any range of angles derivable within these recited angles. Any side arm known to those of ordinary skill in the art may be used, including the most frequent embodiment in which the side arm is constructed of flexible tubing and angle A is therefore variable, and the side arm may be provided at its proximal end with a hub, valve, stopcock, any suitable combination of these, or any other fitting suited to accomplishing the reperfusion described in this disclosure. Furthermore, the proximal end (not labeled) of elongated body 41 may be provided with a valve for regulating fluid entering the proximal end of the sheath and around any device positioned in its passageway, such as one of the present catheters (which may take the form of microcatheters).

The side arm passageway has an outer diameter ranging from 2 mm to 5 mm. Side arm 42 has length L, which may range from 1 cm to 30 cm.

Side arm 42 of medical device 40 depicts stopcock 44. Stopcock 44 is configured to regulate the passage of fluid from passageway 43 of elongated body 41 of medical device 40 through passageway 46 of side arm 42 and out of proximal end 45 of side arm 42. When the stopcock is in the open position, proximal end 45 of side arm 42 is in communication with passageway 46 of side arm 42 and passageway 43 of elongated body 41 of medical device 40.

Figure 3:
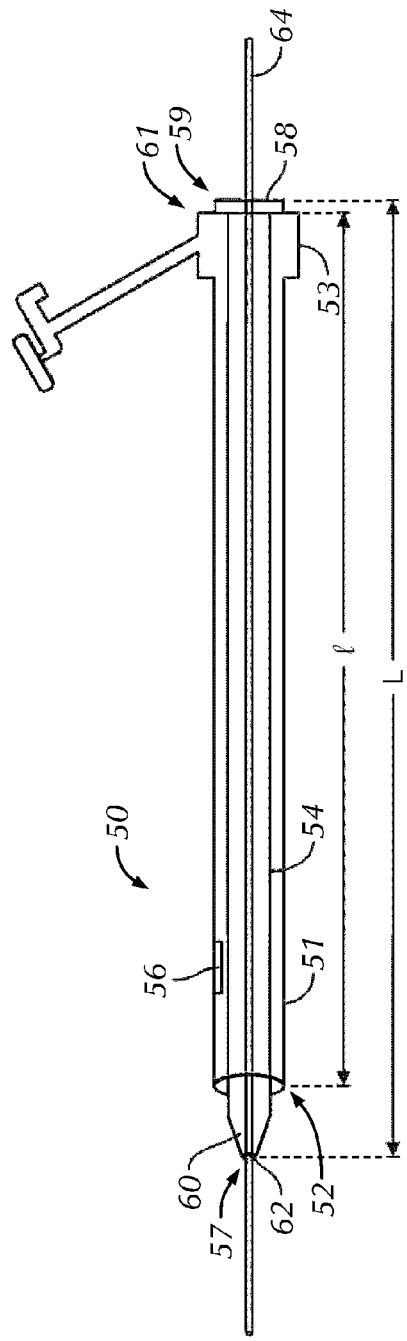
FIG. 3 is a side view of an embodiment of the present medical devices depicting a sheath with an introducer slidably positioned in the sheath passageway and a guidewire slidably positioned within the introducer passageway.

Some embodiments of the present medical devices include an introducer. FIG. 3 depicts an embodiment 50 of the present medical devices that includes introducer 60, a sheath 51, and a guidewire 64. Introducer 60 is slidably positioned in the passageway of elongated body 54 of sheath 51. Introducer 60 includes a tapered distal tip 57 that is configured to facilitate the introduction of medical device 50 into a space in a subject, such as a blood vessel, by facilitating blunt dilation of tissue including a skin surface and a wall of a blood vessel, after a first small incision has been made. A needle is first introduced into the space, a guidewire is introduced via the needle, and the introducer/sheath combination is passed over the guidewire into the space. The introducer gently dilates the channel in advance of the sheath. Introducer 60 includes passageway 62 that extends from the proximal end of introducer 59 to the distal end of introducer 57. Passageway 42 of the introducer has a diameter ranging from 0.5 mm to 5.0 mm.

Introducer 60 is configured to be removable from sheath 51 following introduction of medical device 50 into a target location in a subject.

Introducer length L is the length of the distance between the most distal portion of distal tapered tip 57 and the most proximal portion of proximal end 59. In some embodiments, length L ranges from 10 cm to 140 cm.

In other embodiments, length L ranges from 50 cm to 140 cm. Length L may be any length suitable for the application, including 10 cm, 15 cm, 20 cm, 25 cm, 30 cm, 35 cm, 40 cm, 45 cm, 50 cm, 55 cm, 60 cm, 65 cm, 70 cm, 75 cm, 80 cm, 85 cm, 90 cm, 95 cm, 100 cm, 105 cm, 110 cm, 115 cm, 120 cm, 125 cm, 130 cm, 135 cm, 140 cm, 145 cm, 150 cm, 155 cm, 160 cm, or any range derivable within any of the aforementioned lengths.

Sheath length 1 is the distance between the distal end of sheath 51 and proximal end 61 of sheath 51. A valve, shown schematically as an enlarged portion, may be coupled to the elongated body of the sheath and define the sheath's proximal end. Sheath length 1 may range from 10 cm to 160 cm. In some embodiments, sheath length 1 ranges from 60 cm to 140 cm. In further embodiments, sheath length 1 ranges from 80 cm to 140 cm. In other embodiments, sheath length 1 ranges from 100 cm to 140 cm. Sheath length 1 may be any length suitable for the application, including 10 cm, 15 cm, 20 cm, 25 cm, 30 cm, 35 cm, 40 cm, 45 cm, 50 cm, 55 cm, 60 cm, 65 cm, 70 cm, 75 cm, 80 cm, 85 cm, 90 cm, 95 cm, 100 cm, 105 cm, 110 cm, 115 cm, 120 cm, 125 cm, 130 cm, 135 cm, 140 cm, 145 cm, 150 cm, 155 cm, 160 cm, or any range derivable within any of the aforementioned lengths.

In some embodiments, sheath elongated body 54 may have a uniform outer diameter along the region between its distal end 52 and the junction point of the sheath elongated body with the distal portion of the hub 53, and in other embodiments it may have an outer diameter that varies along this region. The outer diameter of the sheath may range from 4 French (1.3 mm) to 12 French (4 mm). In some embodiments, the outer diameter of the sheath ranges from 4 French to 7 French. In some embodiments, the outer diameter of the sheath ranges from 4 French to 6 French. The outer diameter of the sheath may have any diameter suitable for the application, including 4 French, 5 French, 6 French, 7 French, 8 French, 9 French, 10 French, 11 French, 12 French, or any range of outer diameters derivable within these specific outer diameters.

Sheath 51 includes a sheath passageway sized to accommodate introducer 60 and, subsequently, a catheter configured to advance through an obstruction. Sheath 51 also includes a pressure sensor 56. Pressure sensor 56 is not in contact with the passageway of the sheath. Pressure sensor 56 is configured to detect a fluid pressure and output one or more signals representative of the detected fluid pressure in the manner previously discussed.

The present medical devices optionally include a guidewire. Medical device 50 includes guidewire 64 that is shown slidably positioned within passageway 62 of introducer 60. The length of guidewire 64 will depend on the length of medical device 50 and the application for which the medical device is intended. In some embodiments guidewire 64 has a length that ranges from 25 cm to 150 cm.

The proximal end of introducer 60 is configured to include portion 58 that provides for positioning and stabilization of the introducer within elongated body 54 such that tapered distal tip 57 of introducer 60 extends to a fixed position distal to distal end 52 of elongated body 54. Alternatively, portion 58 may not be used and the sheath may have a locking mechanism capable of clamping the introducer such that it cannot move relative to the sheath.

Any suitable guidewire known to those of ordinary skill in the art may be used for guidewire 64. Non-limiting examples of materials that may be included in the guidewire include stainless steel, nitinol, tantalum, platinum, cobalt alloy, titanium, gold, a biocompatible metal alloy, iridium, silver, tungsten, and combinations of these materials.

In some embodiments of the present medical devices that include a sheath and an introducer, the medical device further includes a catheter. For example, the catheter may be a device as depicted as in FIG. 1A or FIG. 1B, and, depending on its size, may be characterized as a microcatheter.

In some embodiments, the catheter is configured to insulate whatever occupies its passageway, so as to minimize heat transfer to, e.g., fluid flowing through the catheter's passageway. Any catheter known to those of ordinary skill in the art that is configured to thermally insulate the contents of its passageway may be used in this regard. For example, the catheter may include one or more coatings of material on a region of the elongated body of the catheter or on a region of the inner wall defining the passageway of the catheter. In some embodiments, the catheter includes a region that includes a plurality of spaces that are configured to thermally insulate the catheter passageway. One such embodiment is depicted in FIG. 4, which shows a cross-section of one catheter 80 that includes a plurality of spaces 82 within the catheter wall. In some embodiments, the catheter is configured to provide for infusion of a cooling solution within the wall of the catheter, thus providing for maintenance of a relatively cool temperature within the passageway of the catheter. In this manner, the infusion of cooled blood or fluid through the passageway of the catheter may be facilitated.

A further embodiment of the present medical devices is depicted in FIGS. 5A and 5B. FIG. 5A depicts medical device 100, which includes first sheath 101 that includes first sheath elongated body 108 having a first sheath elongated passageway, distal end 109, and proximal end 111 coupled to valve 105. Medical device further includes a second sheath 102 that includes a second sheath elongated body 112 having a second sheath passageway, a distal end 103, and a proximal end 113. Proximal end 113 is coupled to a hub 104. In other embodiments, hub 104 is integral to proximal end. The first sheath and the second sheath each have a length extending from the distal end of the respective elongated body to the proximal-most exposed portion of the respective elongated body. The length of first sheath 101 is greater than the length of second sheath 102. In embodiment 100, second sheath 102 is coupleable to first sheath 101 so that, in use during a procedure, the distal end of the second sheath will be proximal to the distal end of the first sheath. Any suitable means may be used to couple the two sheaths, including co-extrusion or attachment of separate sheaths using any suitable compound or structure, such as a clip, band, glue, or the like.

Medical device 100 also includes catheter 110, which is configured to be positionable in the passageway of first sheath 101. Catheter 110 includes distal end 115 and proximal end 116. Catheter 110 also includes a hub 114 coupled to proximal end 116. In other embodiments, the hub is integral with the catheter. Catheter 110 includes pressure sensor 107, and second sheath 102 includes pressure sensor 106. These pressure sensors may be configured to detect fluid pressure as discussed above.

FIG. 5B depicts device 110 showing the introducers in position in first sheath 101 and second sheath 102. First introducer 120 is depicted slidably positioned in the first sheath passageway. Those of ordinary skill in the art will understand that the recitation of a first device being positionable (e.g., slidably positionable) or positioned (e.g., slidably positioned) in a second device (e.g., in the passageway of a second device) does not require that the entire first device be bounded by the second device (or more specifically, by the passageway of the second device); rather, only a portion of the first device need be surrounded by the second device (or, more specifically, the passageway of the second device) for the first device to be positioned in the second device (or, more specifically, in the passageway of the second device) within the meaning of this disclosure. First introducer 120 has tapered distal tip 121, and includes a passageway 122 configured to receive a guidewire. Second introducer 130 is slidably positioned within the second sheath passageway. Introducers 120 and 130 are configured to be removable from the first and second sheaths. The distal tips of second introducer 130 and second sheath 102 are oriented at an oblique angle to the axis of the passageway of the second sheath in order to ease introduction of the second sheath. Furthermore, as FIG. 5B shows, the two distal tips are configured to align with each other to form a substantially flush end surface.

FIG. 5C depicts a cross-section of medical device 100 with introducers in position within the first and second sheath passageways, respectively. Pressure sensor 106 is depicted attached to second sheath 102. First introducer 120 positioned within the passageway of first sheath 108, and second introducer 130 is positioned within the passageway of second sheath 102.

Embodiments of the present medical devices, sheaths, catheters, and introducers may be fabricated of any substance or mixture of substances known to those of ordinary skill in the art. In some embodiments, the present medical devices, sheaths, catheters, and introducers are at least in part made of a polymeric material. Non-limiting examples of materials include polyether block amides, polyethylene, polyamide, polytetrafluoroethylene, silicone, polyvinylchloride, polyurethane, polyethyleneterephthalate, polypropylene, or copolymers, polyacrylonitrile, polyvinylacetates, polylacticacids, starch, cellulose, polyhydroxyalkanoates, polyesters, polycaprolactone, polyvinylalcohol, polystyrene, polyethers, polycarbonates, polyamides, poly(acrylic acid), Carboxy Methyl Cellulose (CMC), protein based polymers, gelatine, biodegradable polymers, cotton, latex, silicone, polytetrafluoroethene, polyvinylchloride, polycarbonate, Acrylonitrile Butadiene Styrene (ABS), polyacrylate, polyolefins, polystyrene, rubbers, carbon, carbon fiber, cellulose acetate, cellulose nitrate, silicone, polyethylene teraphthalate, polyorthoester, polyanhydride, polyether sulfone, polycarbonate, polypropylene, polytetrafluoroethylene, polylactic acid, polyglycolic acid, a polyanhydride, polycaprolactone, polyhydroxybutyrate, and combinations or mixtures thereof. Some embodiments of the present medical devices include a metal component. Non-limiting examples of such metals include stainless steel, nitinol, tantalum, platinum, cobalt alloy, titanium, gold, a biocompatible metal alloy, iridium, silver, tungsten, and combinations thereof.

The medical devices, sheaths, and catheters set forth herein may be inflexible or flexible, as best suited to the application.

Perfusion Systems

The present perfusion systems may be used in perfusing fluid into a space in a subject. The space may be a space that that includes fluid, or a space that is normally occupied by fluid but is depleted of fluid due to an obstruction to fluid flow into the space. For example, the space may be a blood vessel. Fluid may be perfused, for example, downstream of a site of obstruction to fluid flow in a space in a subject.

Figure 6:
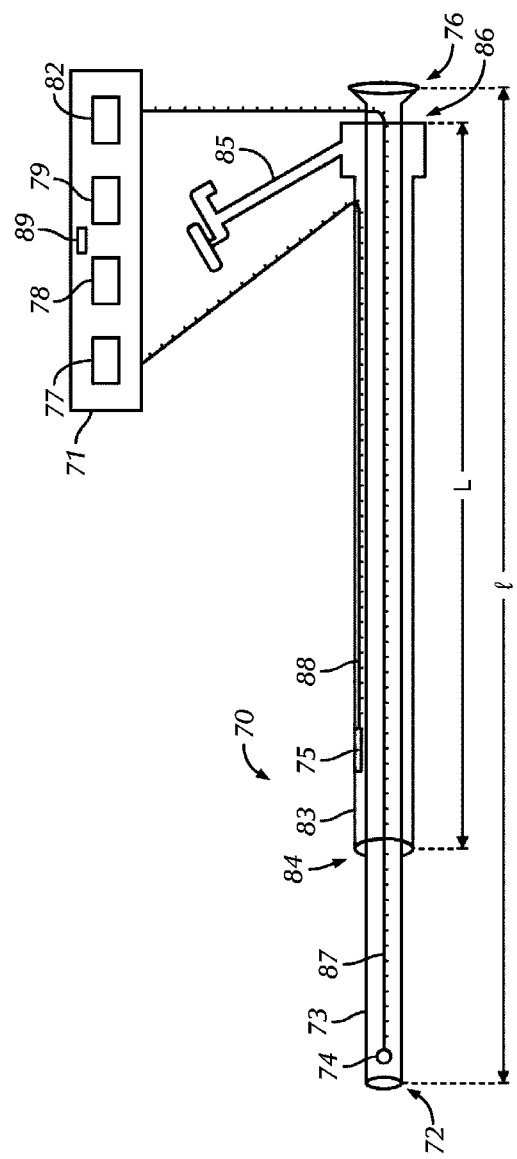
FIG. 6 is a side view of an embodiment of the present perfusion systems, depicting a sheath with a sheath pressure sensor, a catheter (having a catheter pressure sensor) positioned within the sheath passageway, and schematically-depicted leads extending from the pressure sensors to a device that includes a detector system for receiving one or more signals from each of the sensors.

FIG. 6 depicts one embodiment of the present perfusion systems. Perfusion system 70 includes one of the present medical devices, which includes sheath 83 having an elongated body with distal end 86. Sheath 83 includes sheath pressure sensor 75 attached to the elongated body of the sheath near distal end 84 of sheath 83. Perfusion system 70 further includes catheter 73 that is configured to be slidably positioned within the passageway of sheath 83. Catheter 73 includes catheter pressure sensor 74 attached to the elongated body of the catheter near the distal end of catheter 72. The proximal end of the elongated body of catheter 73 includes a hub portion 76. Hub portion may be attached separately to the elongated body of catheter 73 or it may be integral with the elongated body of catheter 73. Sheath length L and catheter length 1 are depicted.

In the embodiment depicted in FIG. 6, lead 87 is attached to catheter pressure sensor 74 and device 71, and lead 88 is attached to sheath pressure sensor 75 and device 71. The pressure sensors are each configured to detect a fluid pressure, and to provide a signal or signals that is representative of the detected fluid pressure. as discussed above. Leads 87 and 88 (as well as the leads depicted in FIG. 7) are graphic/schematic representations of an embodiment of the present medical devices in which power and signals representative of detected fluid pressures are transmitted to and from the sensors in a wired manner.

Device 71 includes a power source 77 that transmits power through leads 87 and 88 to catheter pressure sensor and sheath pressure sensor, respectively. For a sensor that is fiber optic, that "power" may be a transmitted light signal. A signal (or signals) representative of the detected fluid pressure in the sheath pressure sensor and/or the catheter pressure sensor is generated by the respective pressure sensor and transmitted through lead 87 and/or lead 88 to a detector 78 that is configured to receive a signal from one or both pressure sensors and convert (and/or display) the signal(s) to a fluid pressure or a difference in fluid pressure between the detected fluid pressures. For a sensor that is fiber optic, that signal may take the form of light, such as light that is reflected from the sensor (e.g., from the sensor diaphragm). Display 79 receives input from detector 78, and displays the value corresponding to the detected fluid pressure or difference in fluid pressures. Controller 89 transmits the signal to a pump 82. Controller 89 is configured such that when a predetermined pressure from the catheter pressure sensor or a predetermined pressure differential between the catheter pressure sensor and the sheath pressure sensor is detected, the controller activates pump 82. Pump 82 is configured to facilitate the transfer of fluid from side arm 85 of sheath to catheter 73. The controller may also be configured to shut off the pump, not send a signal to the pump, and/or reverse the direction of flow controlled by the pump if the pressure from the catheter pressure sensor is too high (e.g., if it meets or exceeds the pressure detected by the sheath pressure sensor). The controller may be programmed in any suitable manner, including using hardware, firmware, software, or any suitable combination of these. The controller may be configured to be programmed with pump flow rates, cut-off pressures, and the like by the user.

Pump 82 can be configured to transmit fluid from side arm 85 of sheath 83 to catheter 73, or from sheath 112 to catheter 110 (see FIG. 5A), using any method known to those of ordinary skill in the art. For example, pump 82 may be configured to include a roller that becomes activated to transfer fluid through a compressible tubing. Some embodiments include a compressor system for transfer of fluid from a chamber. The end result is transmission of fluid from the relevant sheath (e.g., sheath 83 via side arm 85 or sheath 112) to the relevant catheter (e.g., catheter 72 or catheter 110).

Figure 7:
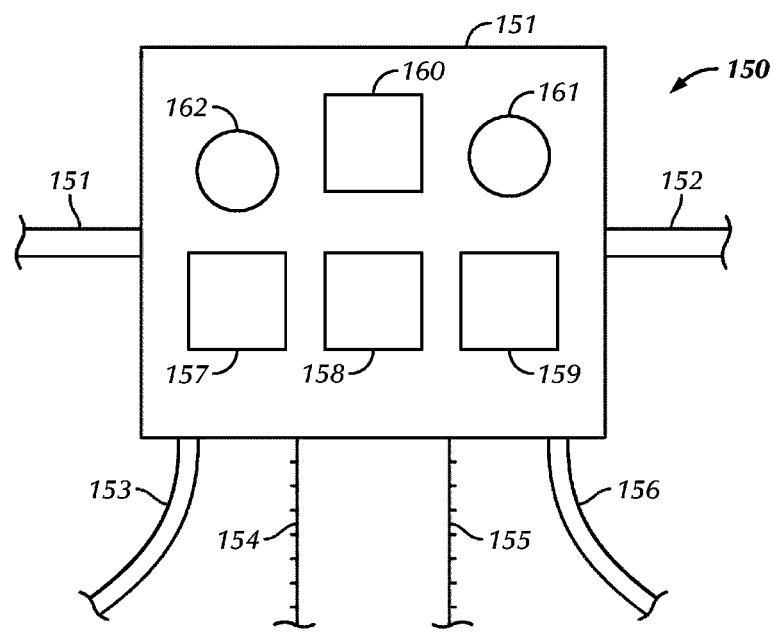
FIG. 7 is a side view of one embodiment of a device of one of the present perfusion systems, which includes a detector system, a pump, a power source, a cooling system, and a control system. The depicted embodiment shows connected tubing for transporting cooling fluid to and from the device, connected tubing for transporting blood to and from a sheath and catheter, and leads attached to the device that are configured to receive signals from the pressure sensors of one of the present medical devices.

FIG. 7 depicts a part of perfusion system 150, another embodiment of the present perfusion systems. Device 151 is shown schematically as including controller 160, power source 157, detector system 158, display 159, pump 156, and thermoregulator 161. Power source 157 is configured to transfer power through schematically-represented lead 154 and lead 155. The power that is transmitted is sufficient to permit detection of a signal corresponding to fluid pressure from the sheath pressure sensor and the catheter pressure sensor. The signals that are generated from the pressure sensors are transferred through lead 154 and lead 155 to detector system 158. Detector system 158, which may include on or more detectors, such that each pressure sensor sends signals to a separate detector, is configured to receive the signals and to convert the signals to a fluid pressure. The detector system (or, more specifically in some embodiments, the individual detectors) transmits this information to display 159, which then displays the fluid pressure to a user. The detector system can also send information to controller 160, which can be configured to activate pump 162 upon detection of a particular magnitude of fluid pressure. Input tube 153 transmits blood from one structure of the present medical devices (e.g., the side arm of a medical device as set forth in FIG. 6 or one of the two sheaths of the medical device shown in FIG. 7) into a chamber in device 151. Thermoregulator 161 provides for a cooling system which cools blood or fluid in the chamber to a specified level. Input tube 151 provides for input of cooled solution or refrigerant into device 151, and output tube 152 provides for output of solution or refrigerant from device 141. Thermoregulator is configured to provide for adjustment of temperature within the chamber by a user. Cooled fluid within the thermoregulator is transmitted from the chamber through a catheter (such as the catheter depicted in FIG. 6 or in FIG. 7) when the pump is activated.

Any thermoregulator, pump, detector system, display and power source known to those of ordinary skill in the art are contemplated for inclusion in the present devices for use with the present perfusion systems.

Kits

Figure 8:
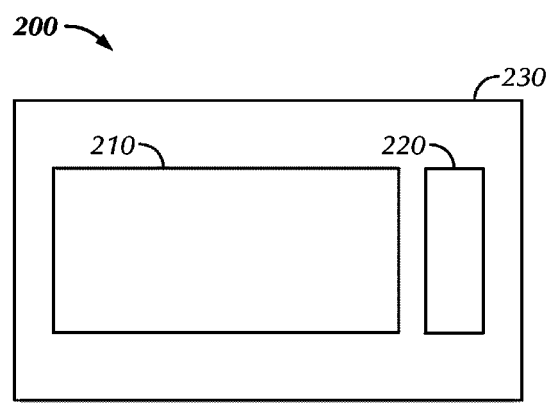
FIG. 8 is a diagram that depicts one embodiment of the present kits that includes sealed packaging containing one of the present medical devices and instructions for use.

Some aspects of the invention concern kits that include any of the present medical devices in suitable packaging. One embodiment of a kit is kit 200, depicted in FIG. 8. Kit 200 includes package 230 that includes sealed container 210 containing medical device 10 set forth in FIG. 1A. Packaging 230 is hermetically sealed.

In some embodiments of the present kits, components of the medical devices or perfusion systems are packaged into separate containers. For example, some embodiments include a kit that includes the medical device, such as device 50 in FIG. 3. For example, introducer 60, sheath 51, and guidewire 64 may be packaged in a first sealed container, a second sealed container, and a third sealed container, respectively. Each of the sealed containers may be included in a single large container or packaged in separate containers. Kit 200 further includes instructions for use 220, that explains how to use the medical device, such as how to use in a procedure for reperfusing blood to an obstructed region of a blood vessel.

Methods

The present methods include any procedure that involves inserting a present medical device and/or perfusion system component into a subject, where a pressure from a pressure sensor of the medical device and/or perfusion system component is detected. Other embodiments of the present methods include inserting one of the present medical devices and/or perfusion system components into a subject, detecting a fluid pressure from the subject from the pressure sensor of the medical device and/or perfusion system component, and inserting a fluid into the subject through a medical device, sheath or catheter of the medical device and/or perfusion system. The present methods further include any procedure that involves using an embodiment of the present perfusion systems to infuse a fluid into a subject.

The subject may be any subject, such as a mammal. In some embodiments, the subject is a human. The subject may be known or suspected to have an obstruction to fluid flow into a space that is normally filled with fluid. For example, the obstruction to fluid flow may be an obstruction to blood flow in an artery or a vein. The obstruction to blood flow may be, for example, a plaque, an embolus, or clot in an artery or vein. The artery or vein may be any artery or vein in a human subject. Nonlimiting examples of arteries include a cerebral artery, a carotid artery, a vertebral artery, a femoral artery, brachial artery, renal artery, coronary artery, or a subclavian artery. In this disclosure, the aorta is an artery.

Figure 9:
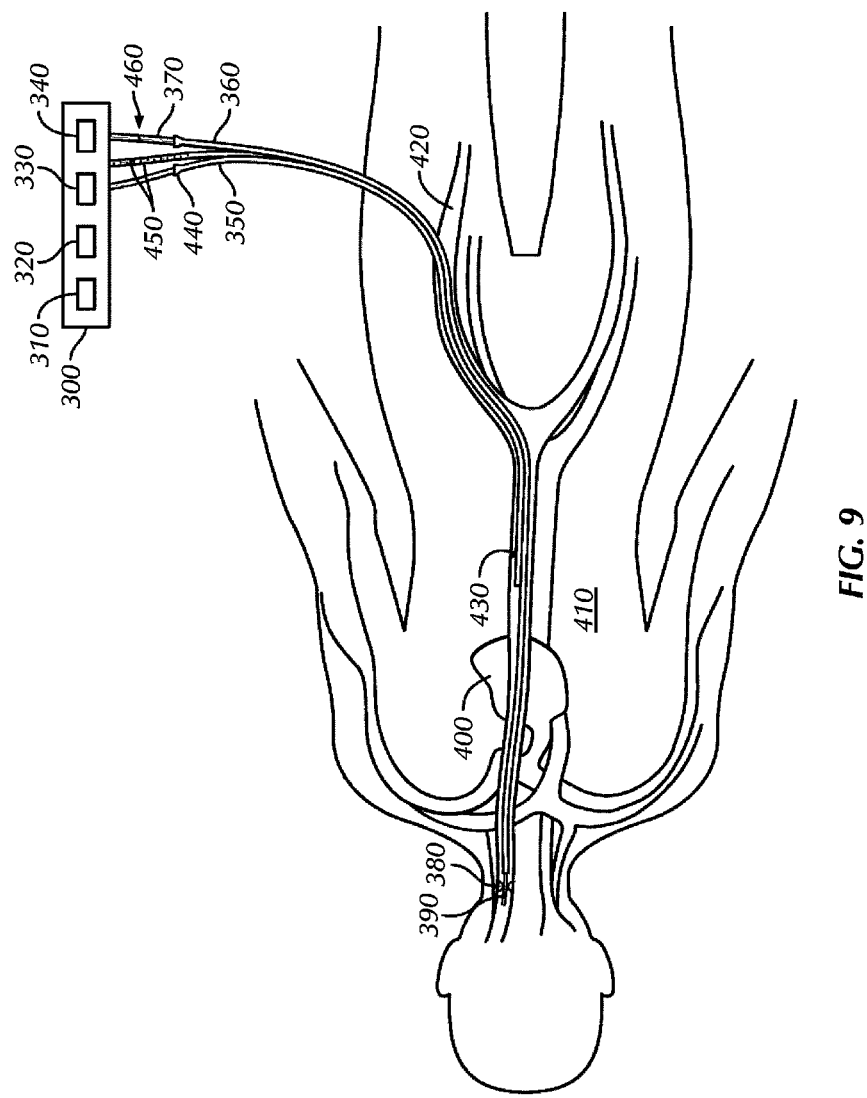
FIG. 9 is a diagram depicting the use of an embodiment of the present perfusion systems to deliver blood to a site located downstream of an obstruction in a carotid artery of a subject.

The present medical devices and/or perfusion system components may be introduced into a subject via any method known to those of ordinary skill in the art, such as percutaneously. In particular embodiments, an introducer is employed to introduce a sheath of the present medical devices or perfusion systems into a blood vessel of a subject. FIG. 9 depicts an example of a subject 410 with an obstruction to blood flow 380 in the left carotid artery. Medical device 300 includes a first sheath 360 and a second sheath 350. A first introducer and a second introducer may be used to insert first sheath 360 and second sheath 350 into the subject. A guidewire (not shown) may then be inserted into the first introducer and advanced through a passageway of the introducer. The introducer may then be removed. Under fluoroscopic guidance, the guidewire may be advanced into subject 410, and then catheter 370 may be advanced over the guidewire and positioned such that the pressure sensor 390 attached to the catheter body is positioned downstream of obstruction 380. Second sheath pressure sensor 430 may be positioned upstream of the obstruction as shown in FIG. 9, or otherwise in a position in which the relevant fluid (blood, in this case) is flowing normally and under normal pressure. A connection between the pressure sensors and device 300 is established through schematically-represented leads 450. Device 300 includes power source 310 for supplying power to the pressure sensors through the leads 450, detector system 320 for detecting signals from the pressure sensors and converting detected signals to fluid pressures, and display 330, which is configured to display the fluid pressures based on data received from the detector system 320. Hub 440 of second sheath 350 is connected to pump 340 of device 300 such that blood from the passageway of second sheath 350 can pass into device 300. The proximal end of the elongated body of catheter 370 is connected to pump 340 of device 300 such that blood that has passed into the device from second sheath 350 can pass into catheter 370 and subsequently downstream of the site of obstruction 380.

In some embodiments, no pump is incorporated into device 300, and blood flow from the sheath to the catheter occurs due to natural pressure differences. In some embodiments, a valve is present that is configured to open upon detection by the detector system of a predetermined fluid pressure from the pressure sensor of the catheter. Opening the valve results in the transmission of blood from the second sheath through the catheter and downstream to the site of the obstruction, as a result of the natural pressure difference between the two locations. In some embodiments, the valve may be manually operated.

Figure 10:
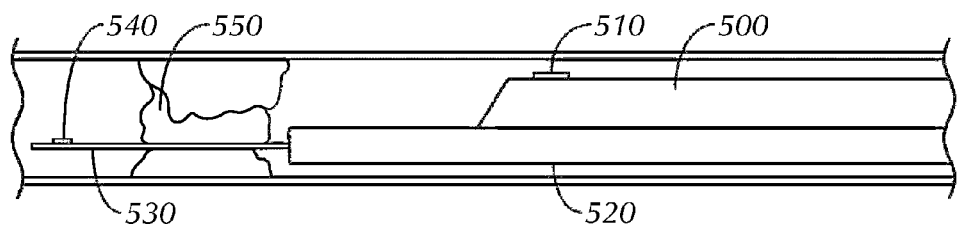
FIG. 10 depicts a side view of the distal end of one embodiment of the present medical devices that has been positioned for reperfusion of blood across a site of obstruction in a blood vessel.

FIG. 10 depicts one embodiment of one of the present medical devices that is configured for reperfusion of blood downstream of an obstruction in a blood vessel. The medical device depicted includes second sheath 500, with pressure sensor 510 attached to the elongated body of sheath 500. First sheath 520 is shown with catheter 530 slideably positioned through the passageway of first sheath 520. Pressure sensor 540 of catheter 530 is positioned downstream (distal, in this embodiment) to the site of the obstruction 550 to blood flow. The pressure sensors transmit signals that are representative of the detected fluid pressures. Depending upon the pressures detected, blood can be transmitted from second sheath 500 to the passageway of catheter 530 and out the distal end of catheter 530, resulting in reperfusion of blood flow downstream of obstruction 550. In some embodiments, the method further includes transmitting cooled blood or fluid through the passageway of the catheter, wherein the temperature of the cooled blood or fluid is below the body temperature of the subject.

The catheter elongated body and/or sheath elongated body may optionally include a region that provides for thermal insulation of the catheter passageway. For example, a fluid that is cooled below the body temperature of a subject may be infused into a space in a subject using the catheter. Thermal insulation of the catheter passageway may facilitate retention of the temperature of the infused fluid. Any method known to those of ordinary skill in the art may be used to insulate the catheter passageway. For example, the catheter elongated body and/or sheath elongated body may include a plurality of spaces that are configured to provide thermal insulation. In some embodiments, the catheter wall (and/or sheath wall) includes channels configured to transfer a coolant through the wall of the catheter (and/or sheath). The medical device may optionally include a pump configured to transfer coolant through the channels in the wall of the catheter and/or sheath. The coolant fluid may be infused through the channels as a closed loop system, thus adding a cooling layer into the wall of the catheter and/or the wall of the sheath. The coolant may be super-cooled even below a freezing temperature, and thus act not only as an insulation but as an actual cooling mechanism.

Additional information concerning cooling systems that can be applied to cool fluids or tissues in the context of the present invention include those disclosed in U.S. Pat. Nos. 7,494,504, 7,485,109, 6,656,209, 6,635,076, U.S. Patent Appl. Pub Nos. 20070043409, 20060089689, 20060052854, 20040147987, 20040068311, 20020007202, and 20010001832, each of which is specifically incorporated by reference.

Figure 11:
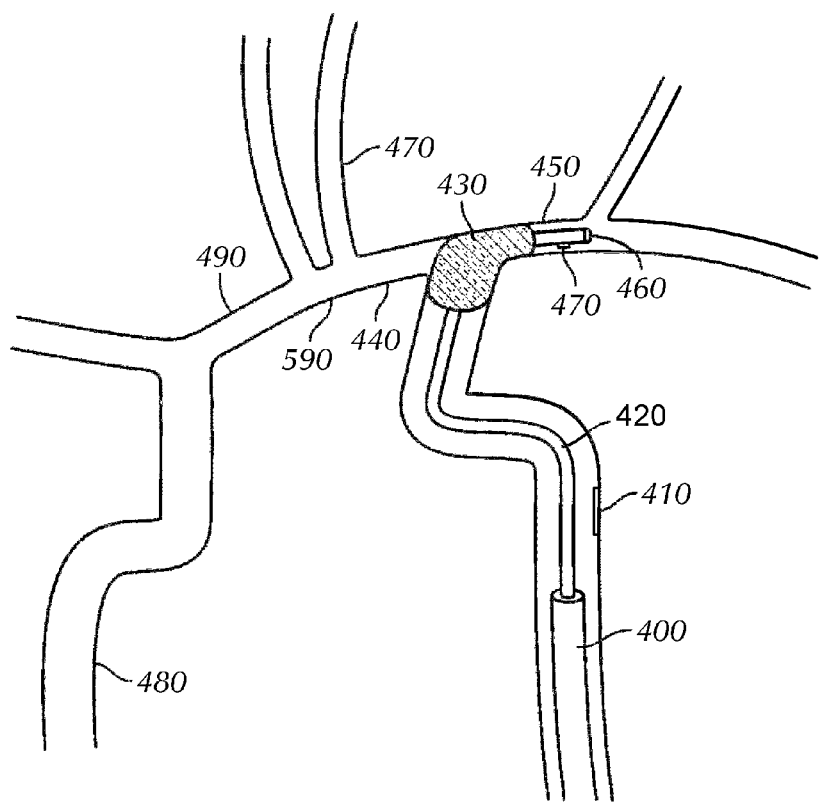
FIG. 11 is a diagram depicting positioning of an embodiment of the present medical devices in a subject with an obstruction of the left middle cerebral artery.

FIG. 11 depicts positioning of an embodiment of the present medical devices in a subject with an obstruction of the left middle cerebral artery. In FIG. 11, sheath 400 has been placed in left internal carotid 410 in the neck of a subject, near the base of the skull. Catheter 420 is passing from the tip of the sheath into the head into the internal carotid, through a thrombus 430 at the bifurcation of the internal carotid into anterior cerebral artery 440 and middle cerebral artery 450. Tip 460 of catheter 420 is in left middle cerebral artery 450, positioned such that tip 460 of catheter and pressure detector 470 on wall of catheter 420 near tip 460 are both downstream to thrombus 430. In this situation, thrombus 430 has blocked flow from left internal carotid 410 into both the left anterior and left middle cerebral artery. However, flow into distal anterior cerebral artery 470 on the left comes from right internal carotid 480 through right anterior cerebral artery 490 and further through anterior communicating artery 590, a normal collateral channel between the two sides of the brain. Therefore, left middle cerebral artery 450 is the target vessel for reperfusion. Any of the foregoing vessels, and any other cerebral vessel not explicitly set forth, are also target vessels for reperfusion within the brain.

Methods for Incorporating One or More Sensors into a Side Wall

In some embodiments, it is desirable to incorporate one or more sensors into the side wall (also characterizable as simply the wall) of a given one of the present medical devices, such as the present sheaths, catheters, introducers and other tubular structures conforming to the present disclosure. The following FIGS. 12A-16B illustrate devices and methods of manufacturing a medical device (e.g., a sheath or a catheter) with one or more sensors (e.g., pressure or temperature sensors) incorporated into its side wall; one of skill in the art will understand that such medical devices include but are not limited to introducer sheaths, diagnostic catheters, multi-lumen catheters, balloon catheters (including those specifically designed for angioplasty), ventriculostomy catheters, and central venous pressure catheters.

Figure 12A:
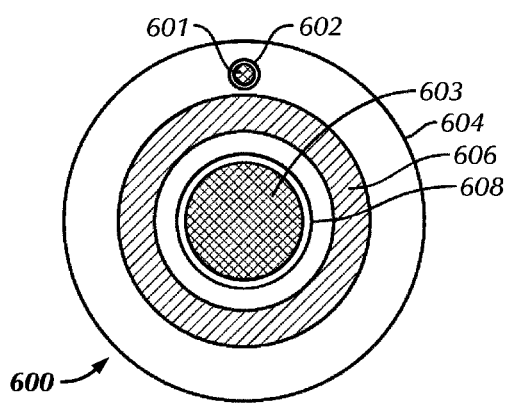
FIG. 12A is a cross-sectional view of one embodiment of a combinations of the constituent parts of one of the present sheaths before heat is applied.
Figure 12B:
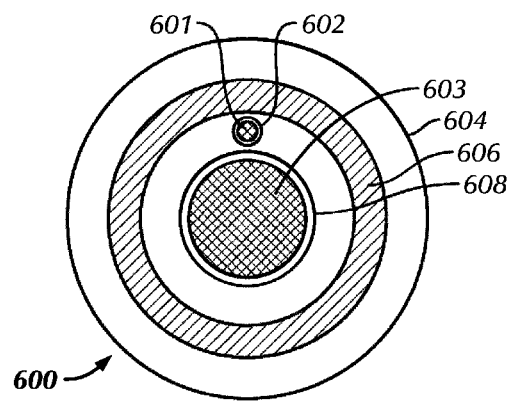
FIG. 12B is a cross-sectional view of another embodiment of a combinations of the constituent parts of one of the present sheaths before heat is applied.
Figure 13:
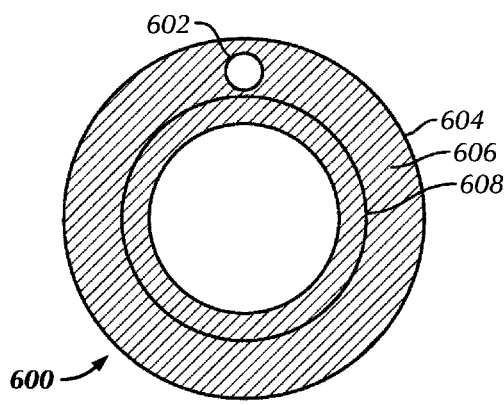
FIG. 13 is a cross-sectional view of one embodiment of a combinations of the constituent parts of one of the present sheaths after heat is applied.
Figure 14:
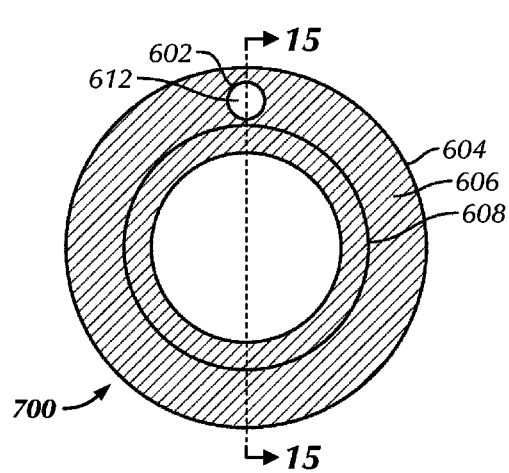
FIG. 14 is a cross-sectional view of one embodiment of one of the present sheaths that is configured to receive a sensor.

FIGS. 12A-14 are illustrative of methods of manufacturing a medical device (which can take the form of a sheath, labeled as sheath 700 in, for example, FIG. 14) with a sensor incorporated into its side wall. FIGS. 12A-12B show cross-section views of two combinations 600 of the constituent parts of sheath 700. The arrangements, or combination, depicted in both of these figures include a first lumen tube 606 that is positioned outside of a first mandrel 603, with a stiffener 608 disposed within first lumen tube 606 and outside first lumen mandrel 603, such that the stiffener is between the first lumen tube and the first lumen mandrel. First lumen tube 606 and stiffener 608 are disposed within a shrink wrap material 604. In some embodiments, as shown in FIG. 12A, a sensor lumen tube 602 is placed between the first lumen tube 606 and the shrink wrap material 604. In other embodiments, as shown in FIG. 12B, sensor lumen tube 602 is disposed between stiffener 608 and first lumen tube 606.

First lumen tube 606 may be comprise any plastic material having a known melting point, including polyether block amides, polyethylene, polyamide, polytetrafluorethylene, silicone, polyvinylchloride, polyurethane, polyethylene-terephthalate, polypropylene, or copolymers, polyacrylonitrile, polyvinylacetates, polylacticacids, starch, cellulose, polyhydroxyalkanoates, polyesters, polycaprolactone, polyvinylalcohol, polystyrene, polyethers, polycarbonates, polyamides, poly(acrylic acid), Carboxy Methyl Cellulose (CMC), protein based polymers, gelatine, biodegradable polymers, cotton, latex, silicone, polytetrafluoroethene, polyvinylchloride, polycarbonate, Acrylonitrile Butadiene Styrene (ABS), polyacrylate, polyolefins, polystyrene, rubbers, carbon, carbon fiber, cellulose acetate, cellulose nitrate, silicone, polyethylene teraphthalate, polyorthoester, polyanhydride, polyether sulfone, polycarbonate, polypropylene, polytetrafluoroethylene, polylactic acid, polyglycolic acid, a polyanhydride, polycaprolactone, polyhydroxybutyrate, and combinations or mixtures thereof. Certain specific embodiments of first lumen tube 606 may comprise PEBAX®. First lumen tube 606 may comprise multiple a single section having a single hardness (e.g., Shore 75D), or multiple sections, such as sections have different (e.g., graduated) hardness values. For example, one embodiment of first lumen tube 606 may a proximal section (such as one that will be approximately ⅔ of the length of sheath 700) that has a hardness of Shore 75D, another section (which can over- or underlap the proximal section) that has a hardness of Shore 45D-55D, and a distal section (which can over- or underlap the 45D-55D section) that has a hardness of Shore 25D-35D. In other embodiments, any desired number of sections may be used to achieve any desired configuration for first lumen tube 606, such as one that has a graduated flexibility from its proximal end to its distal end (e.g., that increases from its proximal end to its distal end). In some embodiments, first lumen tube 606 may include a radiopacifier in any desired amount, such as 45% by weight of barium sulfate.

Stiffener 608 acts to provide structural support to sheath 700. Stiffener 608 may comprise wire or a plurality of wires having a spiral, helical, net, grid, or chicken-wire shape, or such other suitable shape as may provide support to sheath 700 while maintaining the flexibility of sheath 700. For example, in an embodiment suited for producing a 6.0 French version of sheath 700, stiffener 608 may comprise a round, 0.001-inch or 0.0015-inch braid made from 303 stainless steel or 304 ¾ hard stainless steel containing 130 pics per inch. In other embodiments in which stiffener 608 comprises a coil, the coil may be made from a nickel-titanium alloy (e.g., nitinol) flat wire that is 0.0007 inches by 0.003 inches, or from 0.002-inch round stainless steel ¾ hard wire (e.g., 304 ¾ hard stainless steel wire). Either of these wire embodiments may have any suitable pitch, such as 0.002 inches. Stiffener 608 may comprise metals, non-limiting examples of which include stainless steel, nitinol, tantalum, platinum, cobalt alloy, titanium, gold, a biocompatible metal alloy, iridium, silver, tungsten, and combinations thereof. Stiffener 608 may also include other rigid non-metals, including certain polymer-containing materials, such as a para-aramid synthetic fiber (e.g., KEVLAR®). In certain embodiments of sheath 700, stiffener 608 is not necessary for structural support, and therefore may not be used.

Sensor lumen tube 602 may comprise any material capable of containing a pressure sensor. Specific embodiments of sensor lumen tube 602 comprise polytetrafluoroethylene, known under the brand name TEFLON®. Sensor lumen tube 602 may be positioned as in FIGS. 12A-12B using a second mandrel 601 sized to equal or approximately equal to the internal diameter of sensor lumen tube 602. The internal diameter of sensor lumen tube 602 and second mandrel 601 may be less than or equal to 350 microns. Although not shown, an inner first lumen tube, which can comprise the same material as sensor lumen tube 602, may be placed between first mandrel 603 and first lumen tube 606. Sensor lumen tube 602 and such an inner first lumen tube may both be characterized as lumen liners.

The melting point of the material used for sensor lumen tube 602 will be higher, in some embodiments, than the melting point of the material used for first lumen tube 606. The activation point of shrink wrap material 604 is approximately equal to the melting point of the material used for first lumen tube 606. That is, at a given melting temperature, first lumen tube 606 begins to melt, while simultaneously or nearly simultaneously the shrink function of shrink wrap material 604 is activated. For example, in embodiments where first lumen tube 606 comprises PEBAX® and sensor lumen tube 602 comprises TEFLON®, the activation point of shrink wrap material 604 and the melting point of PEBAX® will be around 135 degrees C., while the melting point of TEFLON® will be around 327 degrees C. Shrink wrap material 604 may be FEP (fluorinated ethylene propylene) heat shrink tubing, which, for producing a 6.0 French version of sheath 700, may have an inner diameter of 6 French and an outer diameter of 7.8 French (ID=0.081 inches.+−.0.0005 inches and OD=0.101 inches .+−.0.0005 inches).

First and second mandrels 603 and 601, respectively, may comprise any suitable material, such as silver-plated copper or reusable stainless steel. In an embodiment for producing a 6.0 French version of sheath 700, first mandrel 603 may have an outer diameter of 0.135 inches.

In certain embodiments, combination 600 of first lumen tube 606, stiffener 608, shrink wrap material 604, and sensor lumen tube 602 may be positioned as shown in FIGS. 12A-12B. In other embodiments, mandrels 601, 603 may not be necessary to combination 600, and are not used. In still other embodiments, only one of mandrels 601, 603 may be used in combination 600. Once combination 600 is positioned, combination 600 is heated past the melting point of the material used for first lumen tube 606. For example, where first lumen tube 606 comprises PEBAX®, the melting point will be approximately 135 degrees C. Once the assembly has been brought to or past the appropriate temperature, first lumen tube 606 melts and shrink wrap material 604 shrinks Sensor lumen tube 602 and stiffener 608 are incorporated into the side wall of first lumen tube 606, as shown in FIG. 13. The heating may be accomplished using any suitable technique known to those of ordinary skill in the art, such as through an infrared (IR) heater or heat source.

Figure 15:
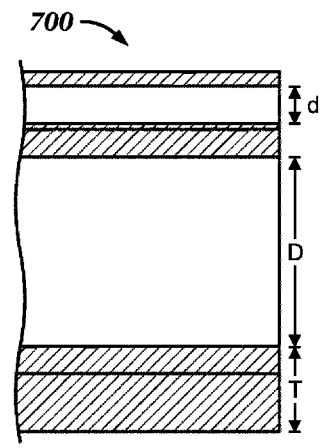
FIG. 15 is a side cross-sectional view of the sheath depicted in FIG. 14.

The assembly is then allowed to cool. Once cool, shrink wrap material 604 is then removed, yielding sheath 700, as shown in FIGS. 14-15. In certain embodiments, mandrels 601, 603 may remain disposed within lumen tubes 602, 606 during the heating and cooling of sheath 700. Mandrels 601, 603 may be removed from lumen tubes 602, 606 once sheath 700 has cooled, or during the cooling period before sheath 700 has completely cooled.

In other embodiments, sheath 700 comprising first lumen 610 and sensor lumen 612 may be formed using extrusion techniques. For example, the lumens may be formed using mandrels, or may be formed using high-pressure air flows.

As a result of these formation steps, sheath 700 comprises a wall 614, a first lumen 610 and a sensor lumen 612. Sensor lumen 612 is independent from first lumen 610, and is further separated from and prevented from impinging into or invaginating first lumen 610 by sensor lumen tube 602. As those of ordinary skill in the art having the benefit of this disclosure will appreciate, multiple side wall lumens may be formed in a given medical device using the techniques described above (including 2, 3, 4, 5, 6 or more), and the passageways forming those lumens may extend the length of the device in question (so as to be exposed or open at both ends) or terminate at any suitable point along the length of the relevant wall.

For an embodiment of sheath 700 that has a length of 5.625 inches, a tapered introducer (such as introducer 60) may be coupled to it for use in a medical procedure that has an introducer length L of 7.5 inches, where the proximal 6.312 inches of the introducer has an outer diameter of 0.079 inches and the distal 1.187 inches tapers from an outer diameter of 0.079 inches to an outer diameter of 0.050 inches at the distal tip of the introducer, and the inner diameter of the introducer is 0.036 inches. Such an introducer may be made from any suitable material, including any of those from which the first lumen tube are made, such as Shore 72D PEBAX®, or GRILAMID®.

As seen in FIG. 15, wall 614 of sheath 700 has a wall thickness T. In certain embodiments, wall thickness T is less than 400 microns, though wall thickness T may, in various embodiments, be less than 350 microns, 300 microns, 250 microns, 200 microns, or 150 microns. First lumen 610 has a diameter D. In certain embodiments, diameter D may, in various embodiments, be less than 600 microns, 550 microns, 500 microns, 450 microns, 400 microns, 350 microns, 300 microns, 250 microns, or 200 microns. Sensor lumen 612 has a diameter d. In certain embodiments, diameter d is less than 350 microns, though diameter d may, in various embodiments, be less than 325 microns, 300 microns, 275 microns, 250 microns, 200 microns, 175 microns, 150 microns, 125 microns, or 100 microns.

Figure 16:
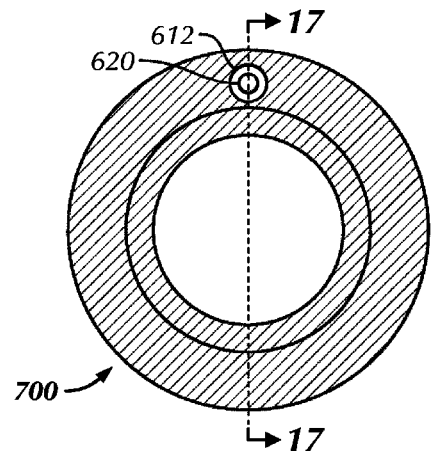
FIG. 16 is a cross-sectional view of the sheath in FIG. 14 in combination with a sensor.

As shown in FIG. 16, a sensor 620 may be inserted into sensor lumen 612 of sheath 700. In certain specific embodiments, sensor 620 comprises a fiber optic Fabry-Perot pressure sensor having a diameter of, or about, 260 microns. Other embodiments of sensor 620 may, in various embodiments, have a diameter of less than 350 microns, 325 microns, 300 microns, 275 microns, 250 microns, or 200 microns. Other suitable sensors or sensor/fiber combinations may be used, such as those described above.

Figure 17A:
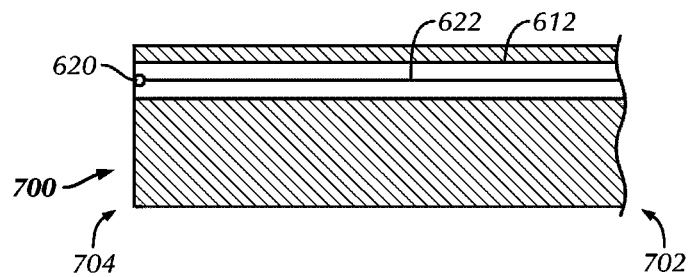
FIG. 17A is a side cross-sectional view of a portion of the sheath depicted in FIG. 16.
Figure 17B:
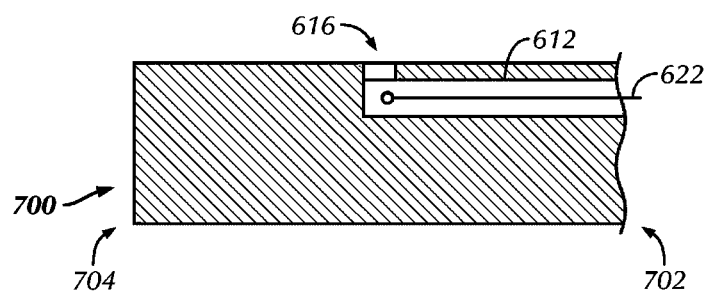
FIG. 17B is a side cross-sectional view of another portion of the sheath depicted in FIG. 16.

Side views of embodiments of sheath 700 are shown in FIGS. 17A-17B, which show portions of a wall of the sheath. For clarity, certain features, such as first lumen 610 and stiffener 608, are not shown. Sheath 700 has a proximal end 702, and a distal end 704. Sensor 620 is coupled to a transmission line 622. At least a portion of sensor 620 and transmission line 622 are secured to sheath 700 or disposed within sensor lumen 612. In some embodiments, as shown in FIG. 17A, sensor 620 may be positioned within sensor lumen 612 at or adjacent to distal end 704 of sheath, such that it can detect a parameter through the opening to the sensor lumen at the distal end of the sheath. In other embodiments, as shown in FIG. 17B, sensor 620 may be positioned within sensor lumen 612 at, near, within, or adjacent to an opening 616 in wall 614 of sheath 700 that is proximal to distal end 704. After the sensor and, if used, the transmission line have been inserted into the sensor lumen, an embedding medium (for example, an epoxy, methacrylate, a curable adhesive (such as one curable with ultraviolet light), or any other suitable medium known to one of ordinary skill in the art) may be inserted into the sensor lumen to secure the sensor and, if used, the transmission line, to the sheath (or relevant medical device). The embedding medium may be used to fix the sensor into a particular position, such as at the distal end of the medical device. The embedding medium may be inserted through any suitable opening that is in communication with the sensor lumen, such as one at the proximal end of the medical device or through an opening formed at any suitable location along the length of the medical device that is in communication with the sensor lumen.

In certain embodiments, sheath 700 may comprise more than one sensor lumen 612, including for example, two, three, or more sensor lumens 612. These additional sensor lumens 612 are positioned in wall 614 of sheath 700 such that sensor lumens 612 are independent from first lumen 610, and are further separated from and prevented from impinging into or invaginating first lumen 610; this prevention is generally a function of the stiffener, but may also or alternatively be a function of the use of sensor lumen tubes 602. Further, sensor lumens 612 may be configured to receive at least a portion of a sensor 620 and at least a portion of a transmission line 622. In various embodiments, the types of sensors 620 and transmission lines 622 used in each sensor lumen 612 may be the same, or may be different from one another.

In certain embodiments, wall thickness T, diameter D, diameter d, or any combination of these dimensions may vary along the length of sheath 700. For example, in some embodiments, T at proximal end 702 of sheath 700 may be greater than T at distal end 704 of sheath 700. As another example, T may vary near the location of a given sensor, such as being slightly thicker adjacent the sensor than at other areas (including those that are circumferentially aligned with the sensor).

Figure 18:
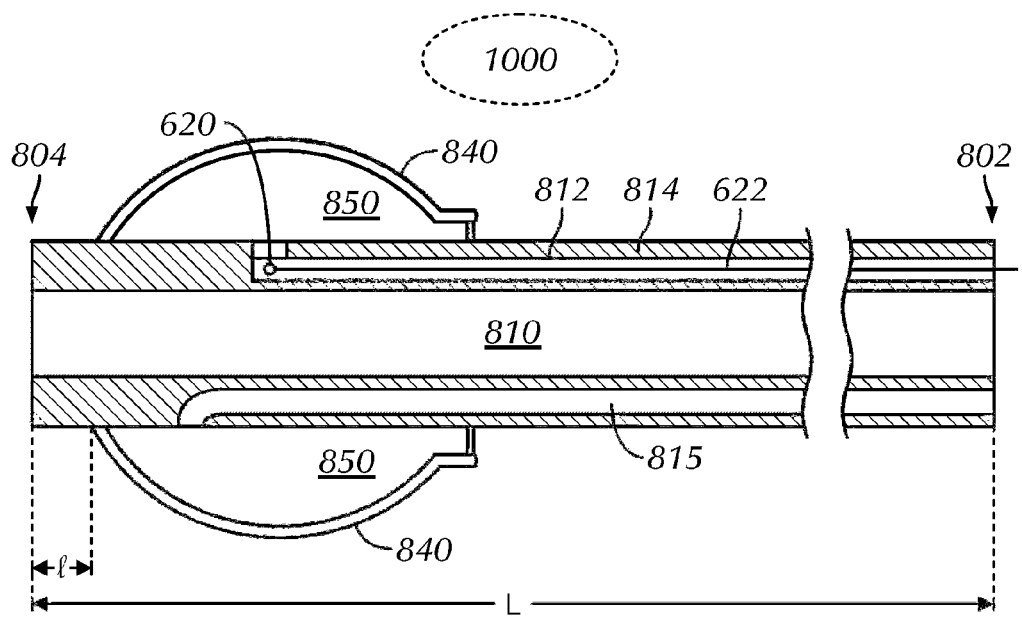
FIG. 18 is a side cross-sectional view of one embodiment of one of the present catheters in combination with a sensor.

Certain embodiments comprise a method for making a catheter, such as the balloon catheter 800 shown in side section view in FIGS. 18A-18B. Balloon catheter 800 may be made in substantially the same way as sheath 700 is made, as described above in relation to FIGS. 12A-17B.

Balloon catheter 800 has a proximal end 802, a distal end 804, a primary lumen 810, and a wall 814. In some embodiments, such as the embodiment illustrated in FIG. 18, balloon catheter 800 further comprises sensor lumen 812 embedded in wall 814. Balloon catheter 800 is configured to be placed in an environment 1000 (e.g., within a blood vessel, within an artery, or within a urethra).

In addition, balloon catheter 800 may comprise one or more balloon membranes 840 forming envelopes 850 between balloon membrane 840 and wall 814. Balloon catheter 800 may have a length L between 3 centimeters and 175 centimeters. In certain embodiments, balloon membrane 840 may terminate at a distance 1 from distal end 804 of balloon catheter 800. In certain embodiments, 1 may be between 2 millimeters and 5 centimeters.

Balloon catheter 800 further comprises an inflation lumen 815 in communication with envelope 850. Inflation lumen 815 is separate from primary lumen 810 and is configured to provide fluid (e.g., air or liquid) to envelope 850. Balloon membrane 840 is configured to expand when fluid is introduced into envelope 850. For example, balloon catheter 800 may be a catheter used to drain urine, such as a Foley catheter. When balloon membrane 840 is inflated, balloon catheter 800 may be held in place in a patient (e.g., the patient's urethra).

Balloon catheter 800 may comprise one or more sensors 620 and transmission lines 622. In the embodiment illustrated, sensor 620 is coupled to transmission line 622. In other embodiments, including those relevant to the present sheaths, sensor 620 may be configured to transmit signals wirelessly, and in such embodiments, transmission line 622 may be unnecessary. Sensor 620 is shown coupled to transmission line 622 and may be disposed at least partially within sensor lumen 812 and positioned proximal to opening 616 in communication with envelope 850. In other embodiments, sensor 622 may be positioned at distal end 804 and in communication with environment 1000. In still other embodiments, sensor 622 may be positioned on the proximal side of balloon membrane 840.

Figure 19:
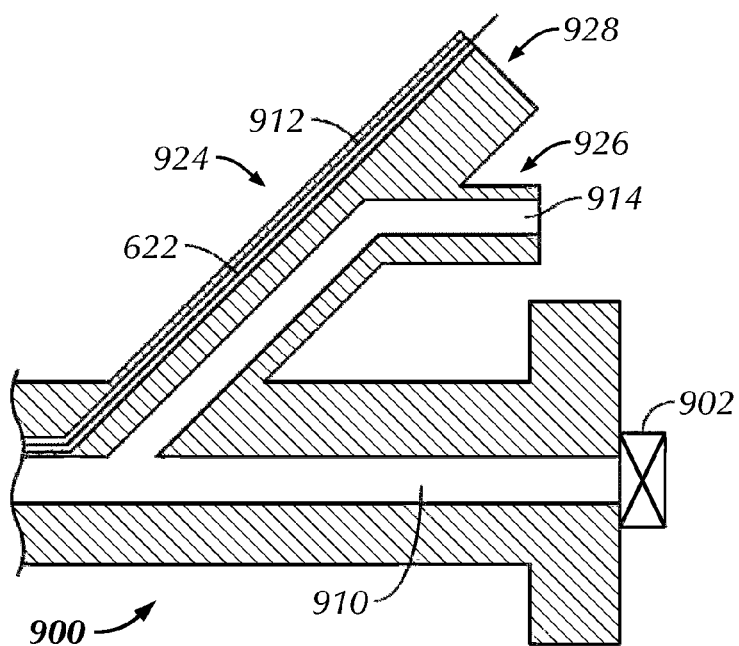
FIG. 19 is a side cross-sectional view of one embodiment of a hub in combination with a transmission line configured to be coupled to a sensor.

In certain embodiments, sheath 700 and catheter 800 may be configured to be coupled to one another, such as through a hub. An example of such a hub 900 is shown in cross-section in FIG. 19. Though the following discussion concerns an embodiment where sheath 700 is configured to be coupled to hub 900, and catheter 800 is configured to be coupled to sheath 700 through a valve of the hub, one skilled in the art will understand that other embodiments may include other tubular members configured for insertion into a patient that may be coupled to hub 900.

Hub 900 may comprise a first lumen 910 configured to be in communication with first lumen 610 of sheath 700, and a sensor lumen 912 configured to be in communication with sensor lumen 612 of sheath 700. Hub 900 may further comprise a valve 902 in some embodiments, where valve 902 is configured to seal first lumen 910, including where catheter 700 is inserted into the lumen of the sheath. Valve 902 is depicted as a graphic symbol positioned outside of hub 900, it should be understood that valve 902 may take the form of a structure that is bound partly or completely by hub 900, such as a valve in the form of a septum (a pierceable, self-sealing member) extending across the proximal entrance to first lumen 910. The valve may be a hemostasis valve. In some embodiments, hub 900 may be characterized as a housing.

Hub 900 may comprise one or more side arms, each side arm having one or more ports. The embodiment depicted in FIG. 19 comprises a side arm 924 comprising a first port 926 and a second port 928. First port 926 comprises a flushing lumen 914 in direct fluid communication with first lumen 910. A stop cock (not shown) may be coupled (e.g., through a flexible conduit) to first port 926 for controlling the flow of fluid through flushing lumen 914.

In the illustrated embodiment, second port 928 comprises sensor lumen 912 in which a portion of transmission line 622 is contained. In some embodiments, transmission line 622 is embedded within hub 900. In certain embodiments, hub 900 or side arm 924 may comprise more than one sensor lumen 912, including for example, two, three, or more sensor lumens 912. These additional sensor lumens 912 are positioned such that sensor lumens 912 are independent from first lumen 910.

In some embodiments, a portion of transmission line 622 is contained or embedded in a second side arm separate from the first side arm. In other embodiments, second side arm 922 comprises a portion of sensor lumen 912, and a portion of transmission line 622 may be contained within sensor lumen 912. The sensor lumens of a given one of the present hubs may be formed according to the methods described above for forming, for example, the present sheaths and catheters, and an embedding medium may be used to secure the respective sensor(s) in place, as described above.

Figure 20:
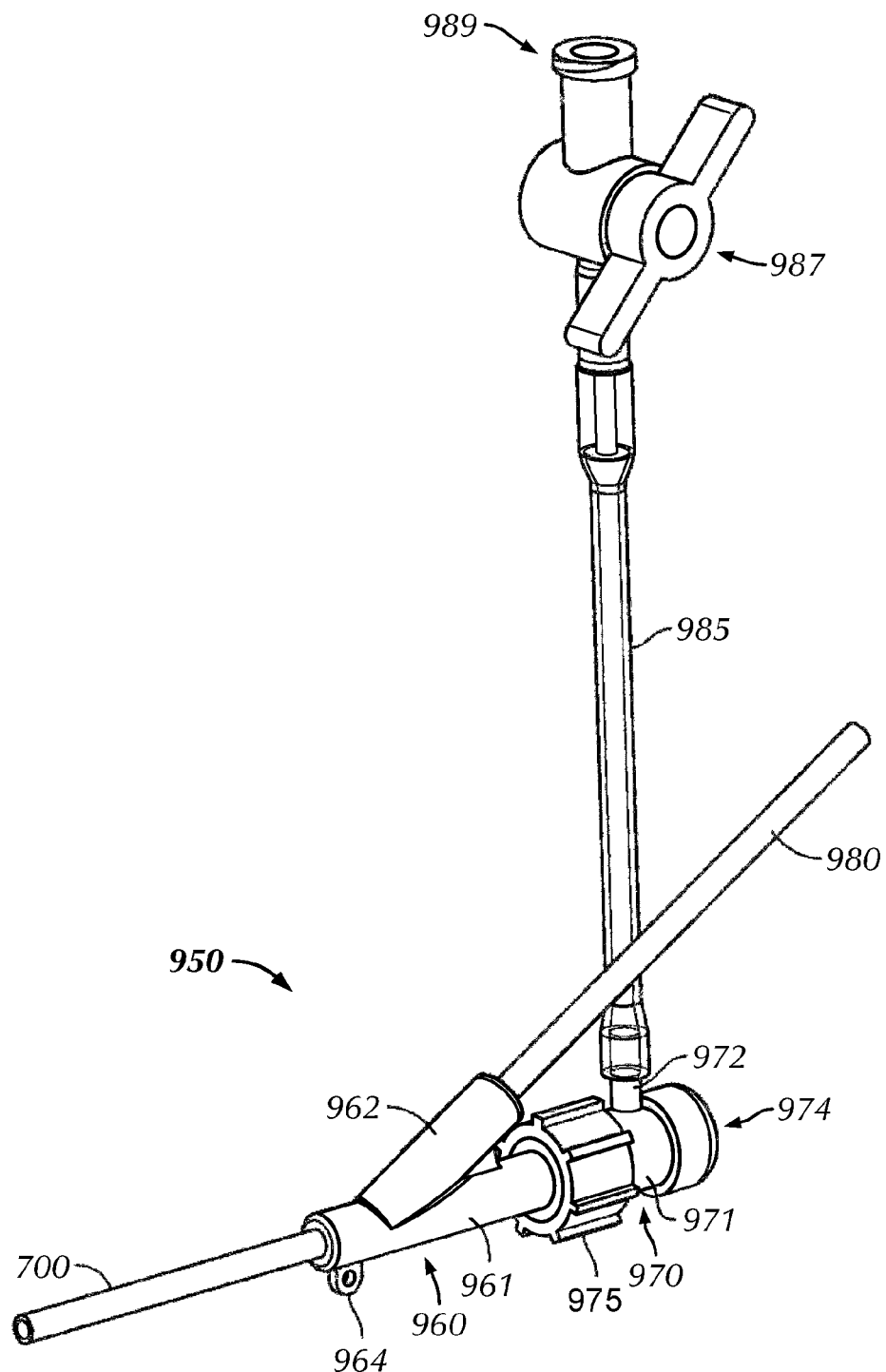
FIG. 20 is a perspective view of a portion of one of the present medical devices that includes one of the present hubs.

The present hubs may comprise multiple pieces coupled together. FIG. 20 shows hub 950, another embodiment of the present hubs that was formed to include a sensor lumen. Hub 950 includes a first (e.g., distal) element 960 that includes a central (e.g., main) segment 951 that is aligned with the medical device (sheath 700, in this embodiment) to which the element is coupled, and first element side arm 962 extending in a proximal direction and that includes a suture opening tab 964, which in the depicted embodiment is located near the distal end of the first element. Angled side arm 962 is oriented at an oblique angle to main segment 951; in the depicted embodiment, the angle between the side arm and the main segment is acute.

First element 960 is coupled to sheath 700 (only a portion of which is shown) and to a second element 970 of hub 950 through a threaded connection. Second element 970 of hub 950 includes a second element side arm 972 that is oriented at a right angle to central (e.g., main) segment 971 of second element 970. Second element 970 also includes valve 974 at its proximal end (the proximal end thus be characterizable as a valved end), which is similar to valve 902 and may take the form of, e.g., a septum. In the depicted embodiment, first element side arm 962 and second element side arm 972 are rotationally offset from each, such as from 5 to 10 degrees. Some embodiments of the present medical devices that include hub 950 may also include a stabilizing element (not shown) that is clipped to the hub and is configured to keep first and second side arms 962 and 972 from rotationally moving with respect to each other. In other embodiments, the two side arms may be aligned (see FIG. 23, described in greater detail below), or offset to a greater extent, such as from 10 to 180 degrees, and any increment in between. Embodiments of the present medical devices that include hub 950 may also include a sensor support conduit 980 that is coupled to first element side arm 962 and that includes a lumen in which a sensor transmission line (e.g., line 622) is embedded (e.g., with an embedding medium). Such embodiments may also include a flush conduit 985 that is coupled to second element side arm 972, a stop cock 987 that is coupled to flush conduit 985 and is configured to control the flow of fluid through the flush conduit and into the main lumen of the hub, and a connector 989 (such as a male luer connector) configured to facilitate the connection of the flush conduit to a fluid source or the like.

Figure 21:
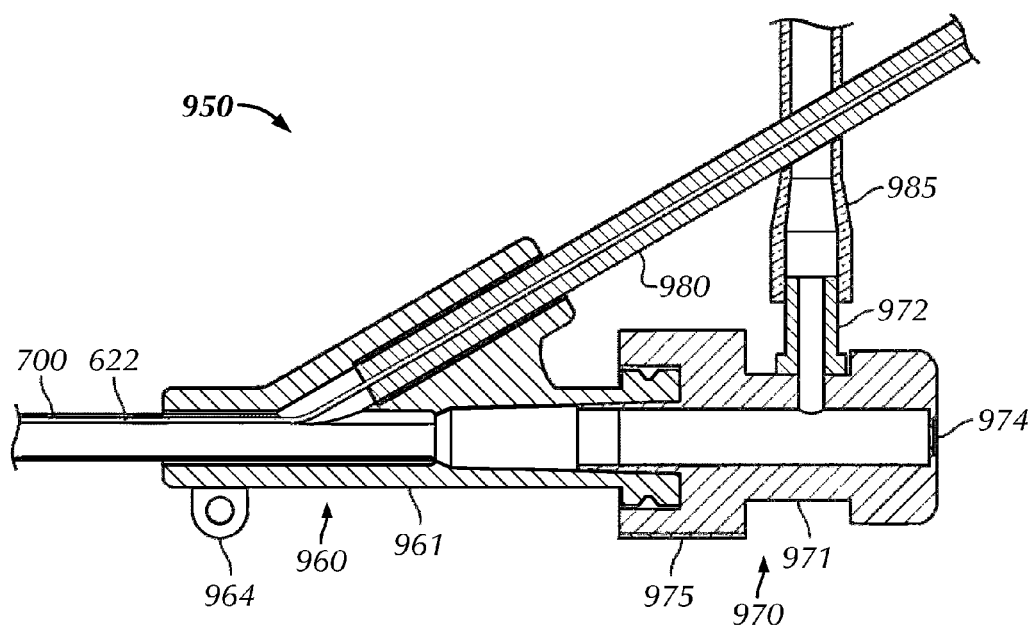
FIG. 21 depicts in cut-away form portions of the structures shown in FIG. 20.
Figure 22:
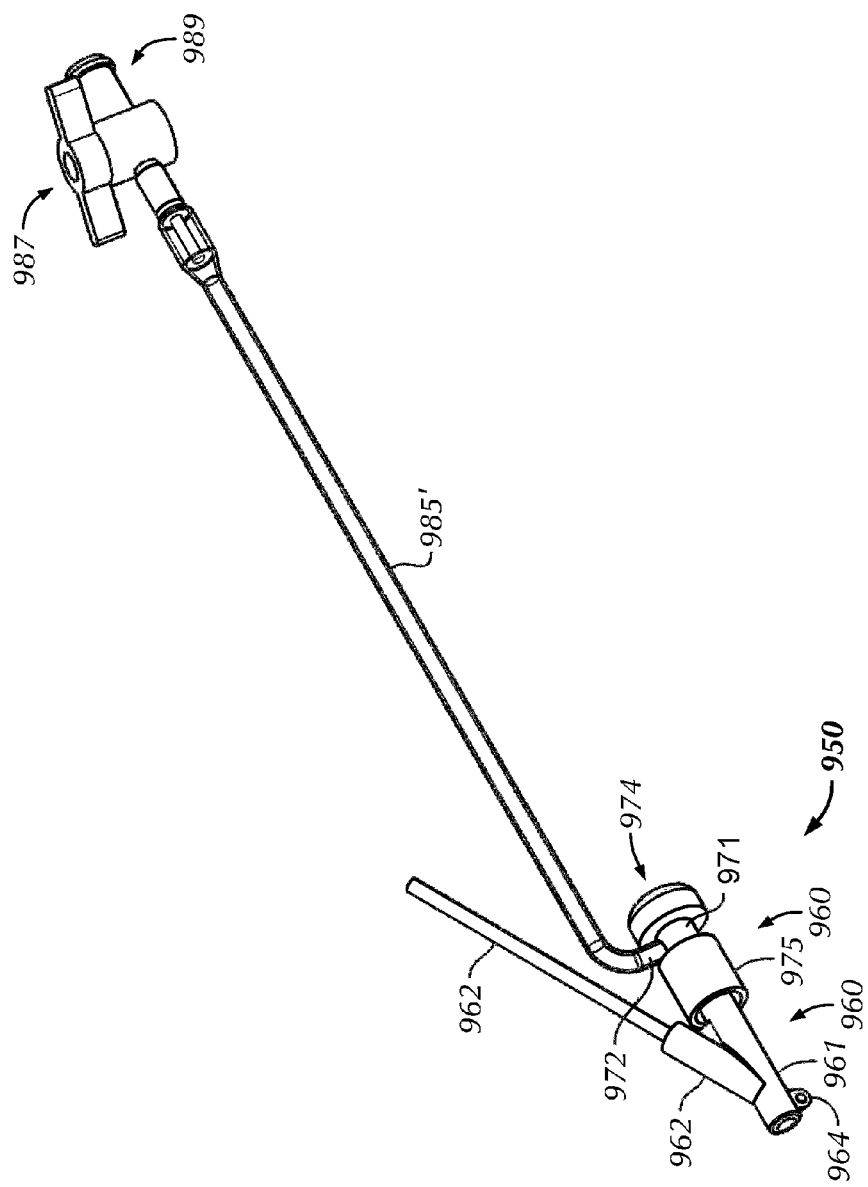
FIG. 22 is a perspective view of a portion of one of the present medical devices that includes another of the present hubs.

FIG. 21 depicts in cut-away form portions of the structures shown in FIG. 20. FIG. 21 also shows the proximal portion of sheath 700 coupled to first element 960 of hub 950 by being positioned in the lumen of central segment 961. This figure also shows line 622 extending from the sensor lumen of sheath 970 out a side port (unlabeled) and into a sensor lumen formed in first element side arm 962, where it then extends into the lumen of sensor support conduit 980 which is coupled to first element side arm 962 in the same way sheath 970 is coupled to first element 960. The connections between the sensor support conduit and the first element and between sheath 970 and the first element of hub 950 may be reinforced in any way known to those of ordinary skill in the art, including through an adhesive, a weld (e.g., one or more sonic welds), heat, and the like. The lumen of first element side arm 962 may vary in size; for example, it may be larger near the proximal end of the side arm to accommodate the insertion of the sensor support conduit, and it may then transition to a lumen that is only as large as or slightly larger than the outside of the sensor transmission line. Flush conduit 985 may be coupled to second element side arm 972 in any suitable way known to those of ordinary skill in the art, including through a friction fit, and may be reinforced as described above. Flush conduit 985 may be oriented as a straight conduit, as shown in FIGS. 20 and 21, or it may be oriented with a bend in it (e.g., a 90 degree bend) as shown via conduit 985' in FIG. 22. Nut 975, which is shown in FIGS. 20 and 21, may be integral with second element 970 when the first and second elements are in a separated state (as shown in FIG. 21) or it may be coupled to either the first or second element when the two elements are in a separated state. Nut 975' may not include exterior ridges, as shown in FIG. 22, in contrast to nut 975.

Figure 23:
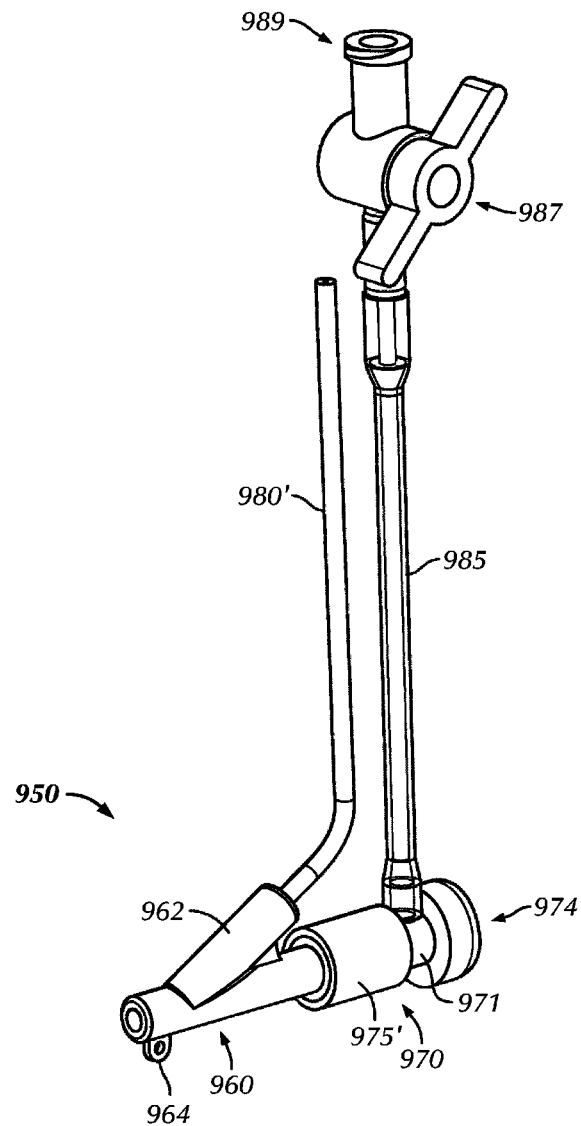
FIG. 23 is a perspective view of a portion of one of the present medical devices that includes yet another of the present hubs.

Other embodiments of the present hubs include multi-piece hubs that include spaced-apart first and second element side arms that are not rotationally-offset from each, as shown in FIG. 23, which depicts a version of hub 950 that is identical to hub 950 depicted in FIGS. 20 and 21 except that the side arms are aligned and nut 975', and that also includes a bent sensor support conduit 980'.

Figure 24:
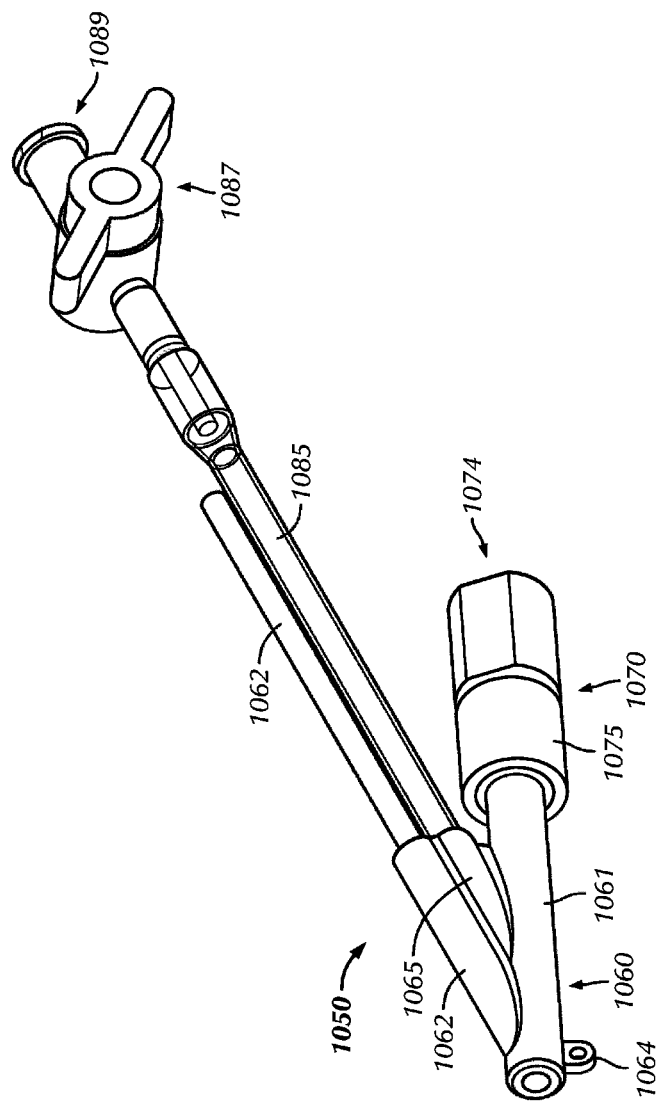
FIG. 24 is a perspective view of a portion of one of the present medical devices that includes still another of the present hubs.

Another embodiment of the present hubs that includes side arms configured for a sensor transmission line and a flush line that are aligned and that share the same angle relative to main segment of the hub is shown in FIG. 24, which depicts hub 1050 that includes a first element 1060 that includes a first side arm 1062 extending at an oblique (acute, in this embodiment) angle from central segment 1061, a suture opening tab 1064 extending from the proximal end of the first element, and a second side arm 1065 positioned proximal to first side arm 1062 and also extending at an oblique (acute, in this embodiment) angle from central segment 1061. Hub 1050 includes a second element 1070 that is coupled to first element 1060 with screw 1075 and that includes a valved proximal end 1074 (the valve, not shown, may for example be a septum) that is configured, like the proximal ends of the hubs depicted in the remaining figures, to be sealingly coupled to another tubular structure, like a catheter. Embodiments of the present medical devices that include hub 1050 may also include a sensor support conduit 1080 that is coupled to first side arm 1062 and that includes a lumen in which a sensor transmission line (e.g., line 622) is embedded (e.g., with an embedding medium). Such embodiments may also include a flush conduit 1085 that is coupled to second side arm 1064, a stop cock 1087 that is coupled to flush conduit 1085 and is configured to control the flow of fluid through the flush conduit and into the main lumen of the hub, and a connector 1089 (such as a male luer connector) configured to facilitate the connection of the flush conduit to a fluid source or the like. Sensor support conduit 1080 and flush line 1085 are coupled to first and second side arms 1062 and 1072, respectively, in the manner described above with respect to the sensor support conduits and flush lines depicted in the other figures, and they serve the respective functions described above with respect to the sensor support conduits and flush lines depicted in the other figures.

The present medical devices, perfusion systems, kits and methods are not intended to be limited to the particular forms disclosed. Rather, they are to cover all modifications, equivalents, and alternatives falling within the scope of the claims. For example, the medical device set forth in FIG. 1A may further include one or more additional pressure sensors. As a further example, the perfusion system set forth in FIG. 6 may further include an introducer for the depicted sheath. Furthermore, in some embodiments it may be advantageous to coat certain surfaces of the medical devices. Any suitable coating could be used, such as one that tends to thwart infection or otherwise make the medical device more acceptable to a living being. The coating may optionally include a therapeutic agent, such as an antibiotic or anticoagulant.

The claims are not to be interpreted as including means-plus- or step-plus-function limitations, unless such a limitation is explicitly recited in a given claim using the phrase(s) "means for" or "step for," respectively.

What is claimed is:
1. An intravascular system comprising:
a sheath comprising a primary sheath lumen and a sensor sheath lumen, the sheath having a sheath length, wherein the sensor sheath lumen terminates at an opening along a distal end of the sheath, the opening located along an exterior of the sheath; and a hub configured to couple to a proximal end of the sheath, wherein the hub comprises:
- a primary hub lumen configured to be placed in fluid communication with the primary sheath lumen when the hub is coupled to the sheath;
- a sensor hub lumen terminating at a sensor port and configured to be placed in fluid communication with the sensor sheath lumen when the hub is coupled to the sheath; and
- a flushing lumen terminating at a flushing port and in fluid communication with the primary hub lumen;

wherein a transmission line is configured to be positioned within the sensor sheath lumen and the sensor hub lumen;

wherein the transmission line is configured to couple to a sensor positioned within the sensor sheath lumen at or adjacent the opening of the sensor sheath lumen along the distal end of the sheath, wherein the sensor is configured to detect a parameter of fluid passing into the opening from a space within a subject;

wherein the primary sheath lumen is separate from the sensor sheath lumen, such that the primary sheath lumen is not in direct fluid communication with the sensor sheath lumen and does not impinge on the sensor sheath lumen along the sheath length; and wherein the primary hub lumen is separate from the sensor hub lumen, such that the primary hub lumen is not in direct fluid communication with the sensor hub lumen.

2. The system of claim 1, wherein the sensor comprises a pressure sensor.

3. The system of claim 1, wherein the transmission line is secured to an interior of the sensor sheath lumen using an embedding medium.

4. The system of claim 1, wherein the sensor comprises a fiber-optic sensor.

5. The system of claim 1, wherein the primary hub lumen is aligned with the sheath primary lumen when the hub is coupled to the sheath.

6. The system of claim 1, wherein the sensor hub lumen is angled relative to the sensor sheath lumen when the hub is coupled to the sheath.

7. The system of claim 1, further comprising a flushing flow control device in fluid communication with the flushing lumen of the hub, wherein the flushing flow control device is configured to regulate a passage of flushing fluid through the flushing lumen and into the primary hub lumen.

8. The system of claim 1, further comprising a primary hub flow control device, wherein the primary hub lumen is configured to be placed in fluid communication with the primary hub flow control device, the primary hub flow control device being configured to seal the primary hub lumen and the primary sheath lumen from an outside environment.

9. The system of claim 8, wherein the primary hub flow control device comprises a valve.

10. The system of claim 8, wherein the primary hub flow control device comprises a self-sealing member.

11. The system of claim 8, wherein the primary hub flow control device is positioned along a proximal end of the hub.

12. The system of claim 8, wherein the primary hub flow control device is positioned at least partially within the primary hub lumen.

13. The system of claim 1, wherein the sheath and the hub form a unitary structure.

14. An intravascular system comprising:
a sheath comprising a primary sheath lumen and a sensor sheath lumen, wherein the sensor sheath lumen terminates at an opening along a distal end of the sheath, the opening being located along an exterior of the sheath;

wherein the sensor sheath lumen is not in direct fluid communication with the primary sheath lumen and does not impinge on the primary sheath lumen.

a hub configured to couple to a proximal end of the sheath, wherein the hub comprises:
- a primary hub lumen;
- a sensor hub lumen; and
- a flushing lumen in fluid communication with the primary hub lumen;

wherein the hub is configured to be coupled to the sheath;

wherein the primary hub lumen is configured to be placed in fluid communication with the primary sheath lumen of the sheath when the hub is coupled to the sheath;

wherein the sensor hub lumen is configured to be placed in fluid communication with the sensor sheath lumen when the hub is coupled to the sheath;

wherein a transmission line is configured to be positioned within the sensor sheath lumen and the sensor hub lumen;

wherein the transmission line is configured to couple to a sensor, the sensor being positioned within the sensor sheath lumen at or adjacent the opening of the sensor sheath lumen; and wherein the sensor is configured to detect a parameter of fluid passing into the opening from a space within a subject.

15. The system of claim 14, wherein the sensor comprises a pressure sensor.

16. The system of claim 14, wherein the transmission line is secured to an interior of the sensor sheath lumen using an embedding medium.

17. The system of claim 14, further comprising a primary hub flow control device, wherein the primary hub lumen is configured to be placed in fluid communication with the primary hub flow control device, the primary hub flow control device being configured to seal the primary hub lumen from an outside environment.

18. The system of claim 14, wherein the sensor comprises a fiber-optic sensor.

19. The system of claim 14, wherein the sheath and the hub form a unitary structure.

* * * * *